United States Patent [19]

Stern et al.

[11] Patent Number: 5,426,097
[45] Date of Patent: Jun. 20, 1995

[54] CALRETICULIN: A NOVEL ANTITHROMBOTIC AGENT

[75] Inventors: David M. Stern, Lake Success; Keisuke Kuwabara, New York, both of N.Y.; Claude Benedict, Houston, Tex.; Jane Ryan, London, United Kingdom

[73] Assignees: The Trustees of Columbia University in the City of New York, New York, N.Y.; Board of Regents, The University of Texas System, Austin, Tex.

[21] Appl. No.: 45,261

[22] Filed: Apr. 6, 1993

[51] Int. Cl.$^6$ .................. A61K 35/42; C07K 15/06
[52] U.S. Cl. .................................. 514/12; 514/21; 530/384; 530/848
[58] Field of Search ............... 514/12, 21; 530/384, 530/848

[56] References Cited

PUBLICATIONS

Sueyoshi, Tatsuya et al., "A new procedure for the separation of protein 2 . . . ", Thrombosis Research, vol. 63, pp. 569–575, 1991.
Abe Hiroshi et al., Molecular Brain Research, vol. 14 pp. 337–343 (1992).
Johnson Robin et al., Molecular Brain Research, vol. 12, pp. 69–76, (1992).
Opas, Michal et al., "Calcium Storage in non–muscle tissue . . . ", Biochem. Cell Biol., vol. 70, pp. 972–979 (1992).
Routsias, J. A. et al, "Calreticulin . . . ", Clin. Exp. Immunol., vol. 91(3), pp. 437–441 (1993) CA119(19):2015996.
Baksh, Shairaz et al., "Expression and purification of recombinant and native calrehiculin," Protein Expression Purification, vol. 3(4), pp. 322–331 (1992). CA117(17):166922m.
Romson, et al., Thrombosis Research (Mar. 15, 1980) 17(6): 841–853.
Gitel, et al., PNAS-USA (Jul. 1977) 74(7): 3028–3032.
Benedict, et al., Circulation Research (Jan. 1986) 58(1): 58–67.
Bush, et al., Faseb J. (Oct. 1990) 4(13): 3087–3098.
Routsias, et al., Clin. Exp. Immunol. (Mar. 1993) 91(3): 437–441.
Benedict, et al., J. Clin. Invent. (Nov. 1991) 88: 1760–1765.
Mookerjee, et al., Immunol. Invest (1993) 22(6&7): 415–429.
Baksh, et al., Protein Express, and Purif. (Aug. 1992) 3(4): 322–331.
Michalak, et al., Biochem. J. (Aug. 1, 1992) 285(3): 681–692.
Fliegel, et al., J. Biol. Chem. (Dec. 25, 1989) 264(36): 21522–21528.

Primary Examiner—Michael G. Wityshyn
Assistant Examiner—C. Sayala
Attorney, Agent, or Firm—John P. White

[57] ABSTRACT

The subject invention provides a pharmaceutical composition, which comprises an amount of calreticulin effective for blocking or preventing thrombosis in a subject, causing substantially no defect or no defect in normal hemostasis, and a pharmaceutically effective carrier. The subject invention provides a method for blocking or preventing thrombosis in a subject, causing substantially no defect or no defect in normal hemostasis, which method comprises administering calreticulin to the subject in an amount effective for blocking or preventing thrombosis. The subject invention provides a pharmaceutical composition, which comprises calreticulin in combination with an other antithrombotic agent, in an amount and proportion effective for enhancing the action of the other antithrombotic agent, to prevent clotting or dissolve clots which have already formed. The subject invention provides a method for enhancing the action of an other antithrombotic agent which prevent clotting or dissolve clots which have already formed, comprising administering to a subject calreticulin in combination with the other antithrombotic agent in an amount and proportion for enhancing the action of the other antithrombotic agent, to prevent clotting or dissolve clots which have already formed.

19 Claims, 27 Drawing Sheets

FIGURE 5

| 1 | 2 | | 3 | 4 |

200—
97.4—
69—
46—
30—
21.5—

200—
97.4—
69—
46—
30—
21.5—

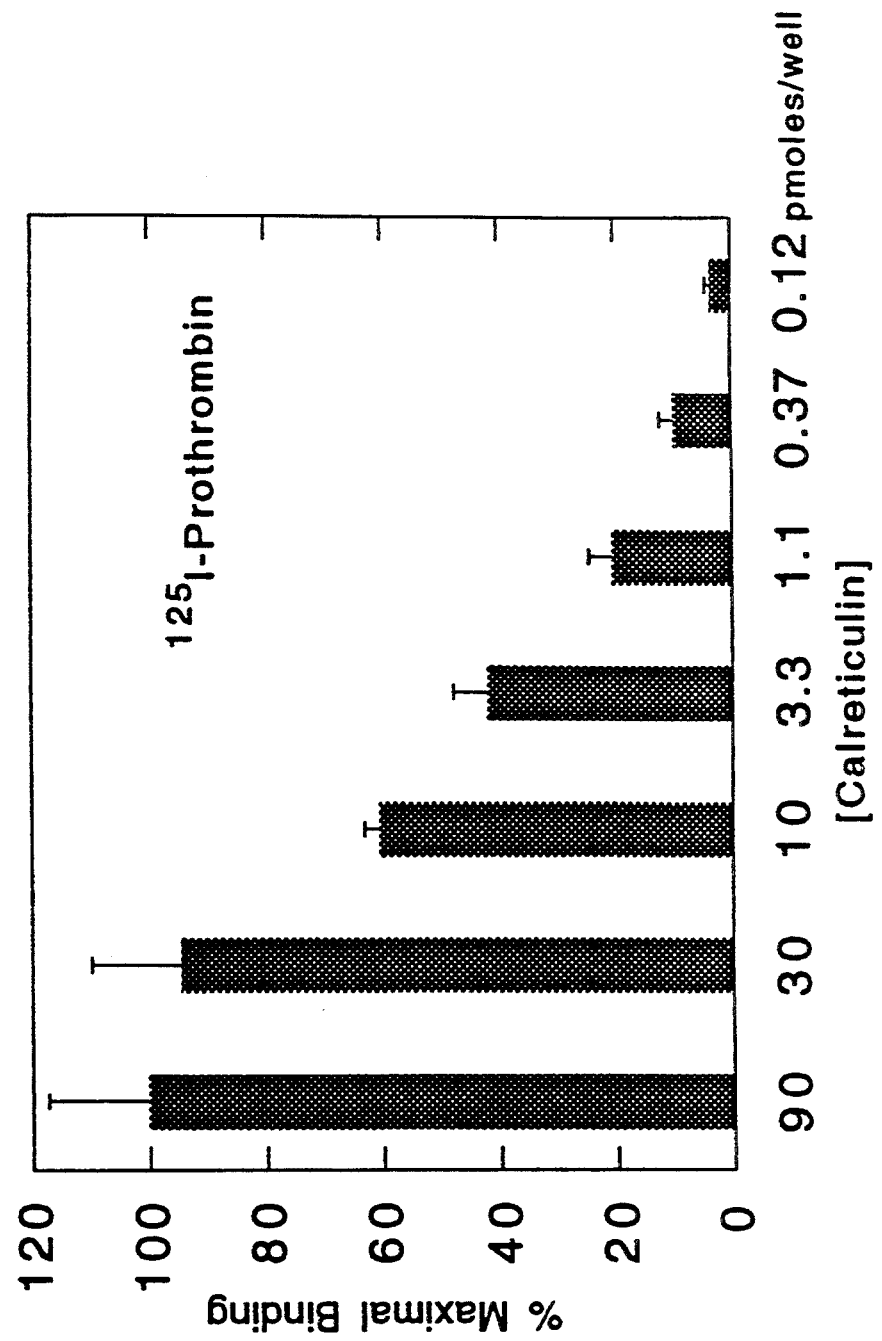

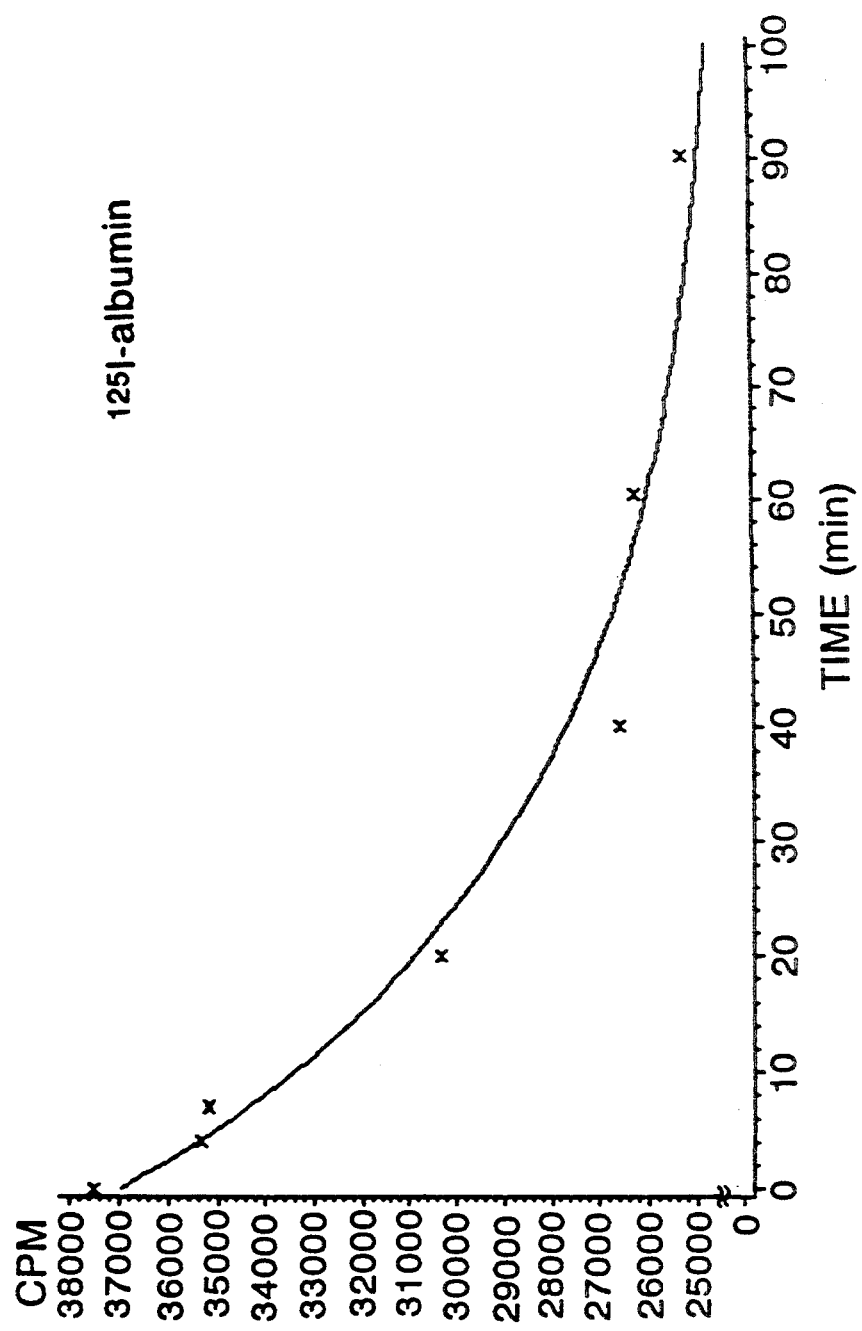

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

Thr Val Tyr Phe Lys Glu Gln Phe Leu Asp Gly Asp
1               5                           10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

Ala Val Tyr Phe Lys Glu Gln Phe Leu Asp Gly Asp
1               5                           10

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

Thr Ile Tyr Phe Lys Glu Gln Phe Leu Asp Gly Asp
1               5                           10

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

Val Val Tyr Phe Lys Glu Gln Phe Leu Asp Gly Asp
1               5                           10

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

Ala Ile Tyr Phe Lys Glu Gln Phe Leu Asp Gly Asp
1               5                           10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
    Thr Ile Tyr Phe Lys Glu Gln Phe Leu Asp Gly Asp
    1               5                   10
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
    Gln Ile Asp Asn
    1
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

```
    Phe Val Leu Ser Ser Phe Tyr Gly Asp Gln
    1               5                   10
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:9:

```
    Ser Gly Thr Ile Phe Asp Asn Phe Leu Ile Thr Asn Asp Glu Ala Tyr
    1               5                   10                      15
    Ala
```

CALRETICULIN: A NOVEL ANTITHROMBOTIC AGENT

The invention described herein was made in the course of work under grant number NIH-HL34625 from the National Institutes Of Health. The United States government has certain rights in this invention.

BACKGROUND OF THE INVENTION

The vitamin K-dependent coagulation Factor IX-/IXa has an important role in hemostasis and can contribute to the pathogenesis of thrombosis (1-4). In view of the well-known rapid clearance of Factor IX from the intravascular space, the association of infused and endogenous Factor IX with the vessel wall (5-6), and in vitro studies demonstrating Factor IX binding to endothelium and platelets (7-9), studies have been performed to characterize the molecular basis of this coagulation protein-cell surface interaction.

At the level of the ligand, the amino terminal gamma-carboxyglutamic acid-containing domain of Factor IX has been shown to be essential for cell surface binding (10-14). At the level of the cell surface site, previous studies have suggested that Factor IX binding involves a protease sensitive polypeptide, which on endothelial cells (ECs) had a predicted Mr of $\approx 150$ kDa (15), and on platelets appeared to involve proteins with Mr's of $\approx 150$ kDa and $\approx 250$ kDa (16).

Abbreviations: EC=endothelial cell; GST=glutathione S-transferase; PVDF=polyvinylidene difluoride; PVC=polyvinlychloride plate binding assay; tPA=tissue plasminogen activator; PAI-1=plasminogen activator inhibitor-1; IC=intracoronary.

To further characterize polypeptides which interact with Factor IX, we employed bovine lung extract as a starting material and purified the major species which binds Factor IX. A $\approx 55$ kDa Factor IX binding polypeptide was isolated which also interacted similarly with Factor X and prothrombin. This polypeptide proved to be identical to calreticulin, a previously described intracellular calcium binding. Interaction of calreticulin/$\approx 55$ kDa with these vitamin K-dependent coagulation factors was localized to the C-domain, but did not change their coagulant properties. In contrast, calreticulin bound to ECs in vitro, was associated with the vessel wall after intravenous infusion, and stimulated production of nitric oxide. Intracoronary administration of calreticulin prevented coronary thrombosis in a canine model without altering plasma clotting times or increasing extravascular bleeding. These results suggest that calreticulin has a novel, potentially useful antithrombotic function.

SUMMARY OF THE INVENTION

The subject invention provides a pharmaceutical composition, which comprises an amount of calreticulin effective for blocking or preventing thrombosis in a subject, causing substantially no defect or no defect in normal hemostasis, and a pharmaceutically effective carrier.

The subject invention provides a method for blocking or preventing thrombosis in a subject, causing substantially no defect or no defect in normal hemostasis, which method comprises administering calreticulin to the subject in an amount effective for blocking or preventing thrombosis.

The subject invention provides a pharmaceutical composition, which comprises calreticulin in combination with an other antithrombotic agent, in an amount and proportion effective for enhancing the action of the other antithrombotic agent, to prevent clotting or dissolve clots which have already formed.

The subject invention provides a method for enhancing the action of an other antithrombotic agent which prevent clotting or dissolve clots which have already formed, comprising administering to a subject calreticulin in combination with the other antithrombotic agent in an amount and proportion effective for enhancing the action of the other antithrombotic agent, to prevent clotting or dissolve clots which have already formed.

BRIEF DESCRIPTION OF THE FIGURES

FIG. 3, Lane 2.SDS-PAGE and gel elution of $\approx 55$ kDa polypeptide derived from lung extract which binds Factor IX; activity profile of material eluted from the indicated slice in lane A.

FIG. 3, Lanes 3 and 4.SDS-PAGE and gel elution of $\approx 55$ kDa polypeptide derived from lung extract which binds Factor IX; the material eluted from slices #5-6 in lane 2 was subjected to nonreduced (lane 3) or reduced (lane 4) SDS-PAGE; Lane 4, activity profile of the material in lane 3.

FIG. 5, Lanes 1, 2, 3, 4.SDS-PAGE of $\approx 55$ kDa polypeptide and purified, recombinant rabbit calreticulin. The $\approx 55$ kda polypeptide purified from bovine lung extract (lanes 1 and 3) or purified recombinant rabbit calreticulin prepared in E. coli (lanes 2 and 4) was subjected to nonreduced (lanes 1-2) or reduced (lanes 3-4) SDS-PAGE. Migration of molecular weight markers is indicated by arrows (numbers indicate molecular masses in kDa).

FIG. 6A, 6B, 6C. Binding of Factors IX, X and prothrombin to recombinant calreticulin; dependence on calreticulin concentration. PVC wells were incubated with the indicated concentration of recombinant calreticulin, excess sites were blocked with albumin-containing buffer, and then a binding assay was performed by adding either $^{125}$I-Factor IX (A), $^{125}$I-Factor X (B) or $^{125}$I-prothrombin (C) alone or in the presence of excess of the respective unlabelled protein. Specific binding is shown.

FIG. 9B. Infusion of recombinant rabbit calreticulin into mice; removal of infused $^{125}$I-albumin from the plasma. Mice were treated as in (A), except that $^{125}$I-albumin was used in place of $^{125}$I-calreticulin.

DETAILED DESCRIPTION OF THE INVENTION

Figure 1A:
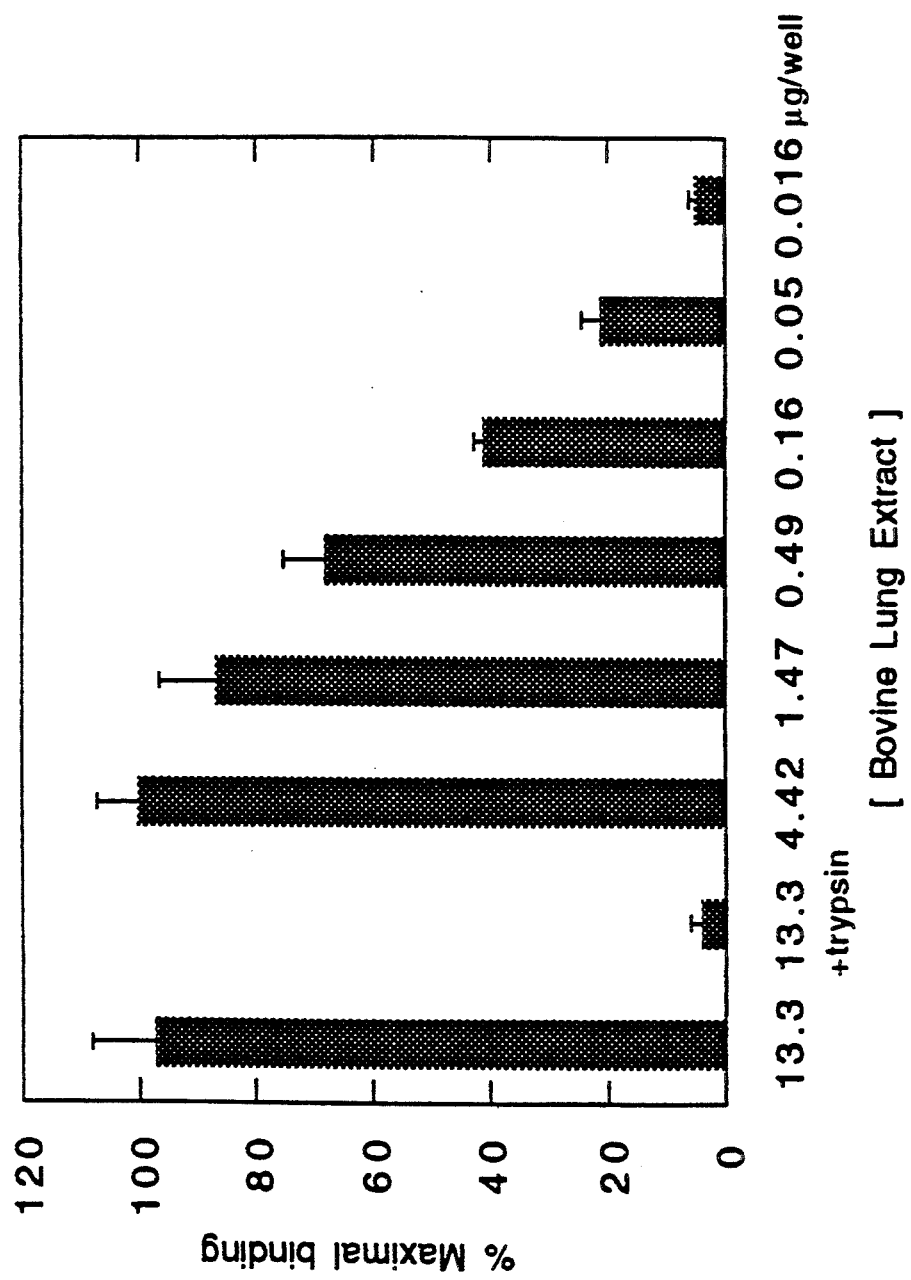
FIG. 1A. Binding of $^{125}$I-Factor IX to lung extract immobilized in PVC wells; dependence on extract concentration.

The subject invention provides a pharmaceutical composition, which comprises an amount of calreticulin effective for blocking or preventing thrombosis in a subject, causing substantially no defect or no defect in normal hemostasis, and a pharmaceutically effective carrier.

Prior to this invention, calreticulin was known only as a regulator of intracellular calcium concentration in the endoplasmic reticulum and sarcoplasmic reticulum; prior to this invention, calreticulin was not known to have any extracellular function.

This invention shows that the effect of calreticulin is in the blood vessel, but not in the circulating blood.

Calreticulin can be used for the prevention of thrombosis and for the treatment of thrombosis.

Normal hemostasis refers to clot formation in response to injury. When hemostasis is normal, the amount of bleeding is normal; when hemostasis is abnormal, the amount of bleeding is excessive.

An advantage of this invention is the fact that calreticulin causes substantially no defect or no defect in normal hemostasis. This makes patient care easier, because there is no or substantially no excessive amount of bleeding. In contrast, other antithrombotic agents cause defects in normal hemostasis. Calreticulin can be used in any medical setting where bleeding is a problem or is expected to be a problem.

The subject invention provides a method for blocking or preventing thrombosis in a subject, causing substantially no defect or no defect in normal hemostasis, which method comprises administering calreticulin to the subject in an amount effective for blocking or preventing thrombosis.

Regarding the method for blocking or preventing thrombosis in a subject, causing substantially no defect or no defect in normal hemostasis, the subject invention provides that the administering may be intracoronary or intravenous.

Intravenous administration has the standard meaning. In particular, intravenous administration means injection into a peripheral vein, for example, a superficial vein, as in the arm or leg.

Intracoronary administration has the standard meaning. In particular, intracoronary administration means injection into the right or left coronary artery. An example of intracoronary administration is injection into the left circumflex coronary artery.

An advantage of this invention is that administration may be intravenous, because other antithrombotic agents can be administered only by intracoronary means. This invention allows for intravenous administration because calreticulin causes substantially no defect or no defect in normal hemostasis.

Regarding the method for blocking or preventing thrombosis in a subject, causing substantially no defect or no defect in normal hemostasis, the subject invention provides that the subject may be a human.

The human may be a patient.

The subject may also include other mammals; examples include dogs, cats, horses, rodents, or pigs, rabbits, among others.

Regarding the method for blocking or preventing thrombosis in a subject, causing substantially no defect or no defect in normal hemostasis, and further regarding the subject wherein the subject is a human, the subject invention provides that the human may be a human at risk for thrombosis; a human who can receive traditional antithrombotic agents but who has not had an effective response to the traditional antithrombotic agent; or a human unable to receive traditional antithrombotic agents.

Traditional antithrombotic agents are those antithrombotic agents which are currently known, and include antifibrinolytic agents, antiplatelet agents, or anticoagulant agents. Examples of known antifibrinolytic agents include streptokinase, tissue plasminogen activator, urokinase, or acylated or other modified forms of plasmin. An example of a known antiplatelet agent is aspirin. Examples of known anticoagulant agents include heparin, warfarin, coumarin derivatives, thrombin inhibitors, or Factor Xa inhibitors.

Regarding the method for blocking or preventing thrombosis in a subject, causing substantially no defect or no defect in normal hemostasis, and further regarding the subject wherein the subject is a human, and additionally regarding a human unable to receive traditional antithrombotic agents, the subject invention provides that the human unable to receive traditional antithrombotic agents is a human undergoing intracranial surgery, or a human with a hemostatic defect. Examples of hemostatic defects include coagulation and platelet disorders.

Calreticulin may be used for humans for whom the use of traditional antithrombotic agents is contraindicated, for example, a human undergoing intracranial surgery, or a human with a hemostatic defect.

Regarding the method for blocking or preventing thrombosis in a subject, causing substantially no defect or no defect in normal hemostasis, the subject invention provides that when the administration is intracoronary, and the subject is a human, then the amount is from about (0.04 mg calreticulin)/(Kg human subject) to about (0.07 mg calreticulin)/(Kg human subject).

Regarding the method for blocking or preventing thrombosis in a subject, causing substantially no defect or no defect in normal hemostasis, the subject invention provides that when the administration is intracoronary, and the subject is a human, then the amount is from about (0.05 mg calreticulin)/(Kg human subject) to about (0.06 mg calreticulin)/(Kg human subject).

Regarding the method for blocking or preventing thrombosis in a subject, causing substantially no defect or no defect in normal hemostasis, the subject invention provides that when the administration is intravenous, and the subject is a human, then the amount is from about (0.2 mg calreticulin)/(Kg human subject) to about (0.4 mg calreticulin)/(Kg human subject).

Regarding the method for blocking or preventing thrombosis in a subject, causing substantially no defect or no defect in normal hemostasis, the subject invention provides that when the administration is intravenous, and the subject is a human, then the amount may be about (0.3 mg calreticulin)/(Kg human subject).

Regarding the method for blocking or preventing thrombosis in a subject, causing substantially no defect or no defect in normal hemostasis, the subject invention provides that this method may comprise the administering of the pharmaceutical composition, which pharmaceutical composition comprises an amount of calreticulin effective for blocking or preventing thrombosis in a subject, causing substantially no defect or no defect in normal hemostasis, and a pharmaceutically effective carrier.

The subject invention provides a pharmaceutical composition, which comprises calreticulin in combination with an other antithrombotic agent, in an amount and proportion for enhancing the action of the other antithrombotic agent, to prevent clotting or dissolve clots which have already formed.

The subject invention provides a method for enhancing the action of an other antithrombotic agent which prevents clotting or dissolves clots which have already formed, comprising administering to a subject calreticulin in combination with the other antithrombotic agent in an amount and proportion effective for enhancing the action of the other antithrombotic agent, to prevent clotting or dissolve clots which have already formed.

Regarding the method for enhancing the action of an other antithrombotic agent which prevents clotting or dissolves clots which have already formed, the subject invention provides that the other antithrombotic agent may be an antifibrinolytic agent.

Regarding the method for enhancing the action of an other antithrombotic agent which prevents clotting or dissolves clots which have already formed, and further regarding the antifibrinolytic agent, the subject invention provides that the antifibrinolytic agent may be streptokinase, tissue plasminogen activator, urokinase, or acylated or other modified forms of plasmin.

Regarding the method for enhancing the action of an other antithrombotic agent which prevents clotting or dissolves clots which have already formed, the subject invention provides that the other antithrombotic agent may be an antiplatelet agent.

Regarding the method for enhancing the action of an other antithrombotic agent which prevents clotting or dissolves clots which have already formed, and further regarding the antiplatelet agent, the subject invention provides that the antiplatelet agent may be aspirin, or an agent which blocks glycoprotein IIbIIIa.

Regarding the method for enhancing the action of an other antithrombotic agent which prevents clotting or dissolves clots which have already formed, the subject invention provides that the other antithrombotic agent may be an anticoagulant agent.

Regarding the method for enhancing the action of an other antithrombotic agent which prevents clotting or dissolves clots which have already formed, and further regarding the anticoagulant agent, the subject invention provides that anticoagulant agent may be heparin, warfarin, coumarin derivatives, thrombin inhibitors, or Factor Xa inhibitors.

Regarding the method for enhancing the action of an other antithrombotic agent which prevents clotting or dissolves clots which have already formed, the subject invention provides that the subject may be a human.

Regarding the method for enhancing the action of an other antithrombotic agent which prevents clotting or dissolves clots which have already formed, and further regarding the human, the subject invention provides that the human is a human at risk for thrombosis; a human who can receive traditional antithrombotic agents but who has not had an effective response to the traditional antithrombotic agent; or a human unable to receive traditional antithrombotic agents.

Regarding the method for enhancing the action of an other antithrombotic agent which prevents clotting or dissolves clots which have already formed, and further regarding the human, and additionally regarding a human unable to receive traditional antithrombotic agents, the subject invention provides that the human unable to receive traditional antithrombotic agents may be a human undergoing intracranial surgery, or a human with a hemostatic defect.

Regarding the method for enhancing the action of an other antithrombotic agent which prevents clotting or dissolves clots which have already formed, the subject invention provides that the administering may be intracoronary or intravenous.

EXPERIMENTAL DETAILS

Summary

Coagulation Factor IX/IXa has been shown to bind to cellular surfaces, and Factor IXa expresses its procoagulant activity by assembling into the intrinsic Factor X activating complex (Factors IXa/VIIIa/X), which also forms on membrane surfaces. We have therefore sought to identify cellular proteins which act by binding Factor IX/IXa. An $\approx 55$ kDa polypeptide was purified to homogeneity from bovine lung extracts based on its capacity to bind $^{125}$I-Factor IX in a dose-dependent and saturable manner. From protein sequence data of the amino terminus and internal peptides, the $\approx 55$ kDa polypeptide was identified as calreticulin, a previously described intracellular calcium binding protein. Recombinant calreticulin bound vitamin K-dependent coagulation factors, $^{125}$I-Factor IX, $^{125}$I-Factor X, and $^{125}$I-prothrombin (Kd's of $\approx 2.7$, 3.2, and 8.3 nM, respectively), via interaction with its calcium binding C-domain, although it did not affect the coagulant properties of these proteins. $^{125}$I-calreticulin also bound to ECs (Kd $\approx 7.9$ nM) via the C-domain in vitro, was found to have an initial rapid phase of clearance in vivo, (and to be associated with the endothelium after intravenous infusion). Exposure of ECs to calreticulin increased production of nitric oxide. In a canine electrically-induced thrombosis model, intracoronary infusion of calreticulin (1.2 mg/animal; N=6; weight of animal is about 22–24Kg) prevented occlusion of the left circumflex coronary artery, without altering plasma coagulation times or increasing bleeding. These results indicate that calreticulin interacts with the endothelium and stimulates release of at least one molecule which interferes with the clotting mechanism, potentially underlying its antithrombotic effect in vivo.

Abstract Of Experiment

A $\approx 55$ kDa, trypsin-sensitive polypeptide was purified from bovine lung extract based on its capacity to bind coagulation Factor IX/IXa in a dose-dependent, saturable manner (Kd $\approx 2$ nM). Protein sequence data, amino terminal and internal, indicated that it was identical to calreticulin. Recombinant calreticulin bound Factor IX in a similar manner, and the binding site was localized to the C-domain, which contains low affinity, high capacity calcium binding sites. Infusion of $^{125}$I-calreticulin to mice demonstrated a rapid phase of clearance, and deposition in the most vascular organs, consistent with in vitro data demonstrating binding of $^{125}$I-calreticulin into cultured endothelial cells (Kd $\approx 4$ nM). These observations led us to test calreticulin as an antithrombotic in an electric current-induced coronary thrombosis model. Intracoronary infusion of calreticulin (single bolus of 1.2 mg/animal; weight of animal is about 22–24 Kg) blocked formation of occlusive thrombi in the left circumflex coronary artery (N=5), whereas saline-treated controls occluded in every case (N=5). Blockade of intravascular thrombosis in animals receiving calreticulin was not accompanied by prolongation of the APTT (activated partial thromboplastic time) or PT (prothrombin time) in coronary sinus or left atrial blood. In contrast, doses of heparin sufficient to prevent coronary thrombosis in this model markedly prolonged the APTT. These data lead us to propose that calreticulin potentially exerts a selective [that is, lack of change in plasma coagulation parameters (PT and APTT) in presence of a blockade of localized coronary thrombosis (canine thrombosis model)] antithrombotic effect.

Introduction

Experimental Procedures

Preparation of reagents: purification of coagulation factora, preparation of recombinant calreticulin, and radiolabelling. Bovine Factors IX, X (a pool of $X_1$ and $X_2$) and prothrombin were purified to homogeneity by previously described methods (17–19), and were supplied by Enzyme Research Laboratories, Inc. (South Bend, Ind.). Factor IX was radiolabelled by the lactoperoxidase method (20) using Enzymobeads (Bio-Rad, Richmond, CA), $^{125}$I-Factor IX was isolated as described (22), and the specific radioactivity was $\approx 2.9 \times 10^4$ cpm/ng. The radioactivity profile of $^{125}$I-Factor IX on SDS-PAGE (10%) showed a single peak with Mr $\approx 55$ kDa. Factor X and prothrombin were radiolabelled by the same procedure to specific radioactivities of $3.4 \times 10^4$ cpm/ng and $2.7 \times 10^4$ cpm/ng, respectively. Bovine serum albumin (Sigma, St. Louis, Mo.) was also radioiodinated by the same procedure to a final specific radioactivity of $1.5 \times 10^3$ cpm/ng. Other coagulation factors, human proteins C and S, bovine Factor Xa, human Factor Va, thrombin and antithrombin III were also obtained from Enzyme Research Labs.

Recombinant rabbit calreticulin and discrete domains from calreticulin were expressed in E. coli using the glutathione S-transferase (GST) fusion protein system with pGEX-3X plasmid (22), as described previously (23). Plasmids containing intact calreticulin, the N-domain (amino acids 1–182), the P-domain (amino acids 182–290), or the C-domain (amino acids 330–401) were expressed in BNN103 E. coli host (23). GST and GST-fusion proteins were purified to homogeneity by one-step glutathione-Sepharose 4B affinity chromatography (Pharmacia, Piscataway, N.J.). In some experiments the GST-full length calreticulin fusion protein was cleaved with Factor Xa, re-applied to glutathione-Sepharose 4B, and the pass-through contained homogeneous recombinant calreticulin. Native rabbit calreticulin was isolated by a selective ammonium sulfate precipitation procedure in the presence of protease inhibitors followed by FPLC Mono Q as described (24). Calreticulin was labelled using the same method for preparing $^{125}$I-Factor IX. Following radiolabelling, $^{125}$I-calreticulin was separated from free iodine by gel filtration, and the final tracer had a specific radioactivity of $3.0 \times 10^4$ cpm/ng, was >95% precipitable in trichloroacetic acid (20%), and migrated as a single band with Mr ≈55 kDa on SDS-PAGE (10%).

Development of assays to detect $^{125}$I-Factor IX binding activity: polyvinylchloride plate binding assay (PVC assay) and EC binding assay. PVC binding assays were performed with lung extracts, partially purified and purified calreticulin. Samples, prepared as described below, were diluted in buffer containing $NaCO_3$ (0.015M; pH 9.2)/$CaCl_2$ (0.1 mM), and 0.05 ml of this material was incubated at 4° C. for 15 hrs in wells of 96-well PVC plates. Then, the mixture was aspirated, the wells were washed once with washing buffer (HEPES, 10 mM, pH 7.55; NaCl, 137 mM; glucose, 11 mM; KCl, 4 mM; $CaCl_2$, 2.6 mM; bovine serum albumin, 0.5 mg/ml) and 0.15 ml of blocking buffer (Tris, 20 mM, pH 7.4; NaCl, 0.1M; $CaCl_2$, 1 mM; bovine serum albumin, 50 mg/ml) was added to each well at 37° C. for 1 hr. After this time, wells were washed again with washing buffer, and 0.05 ml of incubation buffer (Minimal Essential Medium; bovine serum albumin, 5 mg/ml; HEPES, 7 mM, pH 7.3) was added along with $^{125}$I-Factor IX, $^{125}$I-Factor X or $^{125}$I-prothrombin alone or in the presence of a 100-fold molar excess of the respective, unlabelled protein for 2 hrs at 4° C. The medium was then aspirated and each well was washed six times (6 secs total) ice-cold washing buffer (0.15 ml/wash). Bound radioactivity was eluted during a 10 min incubation at 25° C. with elution buffer with Tris (65 mM; pH 7.9), NaCl (175 mM), EDTA (10 mM), and bovine serum albumin (0.5 mg/ml). Where indicated, crude lung extract prepared as above except without protease inhibitors, was incubated with immobilized trypsin (10%, v/v; Sigma) for 1 hr at 37° C. Samples were diluted in buffer containing protease inhibitors as above, and the binding assay was performed. Similar results were obtained when lung extract proteins coated on PVC wells were exposed to trypsin, followed by washing and inactivation of trypsin with protease inhibitors, and then a binding assay was performed as described above.

Equilibrium data were analyzed according to the equation of Klotz and Hunston (25)($B=nKA/[1+KA]$, where B=specifically bound ligand [total binding, wells incubated with tracer alone, minus nonspecific binding, wells incubated with tracer in the presence of excess unlabelled material], n=sites/well, K=the dissociation constant, and A=free ligand concentration) using nonlinear least-squares analysis (Enzfitter). Data showing inhibition of $^{125}$I-Factor IX binding to calreticulin by unlabelled Factors IX, X and prothrombin was fit to the equation (26): $b=B_m[A]K_i/(K_aK_i+K_a[X]+K_i[A])$ , where b=bound radioligand ($^{125}$I-Factor IX); [A]=concentration of radioligand; $K_a=K_m$ in the absence of inhibitor; [X]=concentration of inhibitor (unlabelled Factor IX, X or prothrombin); $B_m$=maximal binding of radioligand in the absence of inhibitor. This representation of binding data is shown in the insets to FIG. 6A–C.

Binding of $^{125}$I-calreticulin to endothelium was studied using confluent endothelial monolayers (0.32 cm$^2$/well). Bovine aortic ECs were prepared and cultured as described previously (21). Wells were washed with elution buffer, washing buffer and incubation buffer, and were then incubated with binding buffer (0.05 ml/well) containing $^{125}$I-calreticulin alone (total binding) or in the presence of a 100-fold molar excess of unlabelled calreticulin (nonspecific binding). Following a 2 hr incubation at 4° C., wells were washed six times rapidly with ice cold washing buffer as above. Where indicated, binding buffer was replaced by washing buffer, except that the amount of calcium chloride or EDTA was varied as stated. Dissociation was studied by the method of infinite dilution (27). Following a binding assay, performed as described above, wells were washed and fresh binding buffer was added for the indicated time. Then, wells were washed once, and residual radioactivity was determined.

Purification of ≈55 kDa polypeptide from bovine lung extract. Bovine lung powder (30 g, Sigma) was added to 300 ml of Tris (20 mM; pH 7.4), NaCl (0.1M), PMSF (1 mM), trasylol (0.1%), and octyl-β-glucoside (1%) for 16 hr at 4° C. with constant mixing. Insoluble material was removed by centrifugation (11,000 g) for 30 min at 4° C., the supernatant (25 g) was filtered (0.45 μm), and applied to hydroxylapatite (300 ml, IBF, Savage, Md.; column equilibration buffer: Tris, 20 mM, pH 7.4; NaCl, 0.1M; octyl-β-glucoside, 0.1%; flow rate, 1 ml/min). The column was washed until the absorbance at 280 nm was <0.01, and was then step-eluted with buffer containing 1M NaCl. This wash was continued until the absorbance was <0.01, and then the column was eluted with $NaPO_4$ (0.5M; pH 7.4). Fractions were collected (5 ml/fraction) and the protein content (OD280 nm) and Factor IX binding activity was determined in the PVC assay (each fraction was tested at 1:100 dilution). Fractions with peak Factor IX binding activity were pooled, dialyzed versus Tris (20 mM; pH 7.4) and octyl-β-glucoside (0.1%) overnight at 4° C., and then applied to FPLC Mono Q (HR5/5; Pharmacia, Piscataway, N.J.). The column was eluted with an ascending NaCl gradient (0.05 to 1M), fractions were collected (1 ml/fraction; flow rate of 1 ml/min), and an aliquot of each was assayed as above. Samples with peak Factor IX binding activity were pooled (≈70 ml), concentrated by centrifugation on Centricon membranes (Amicon, Lexington, Mass.; molecular weight cut-off 10,000)(≈7 ml), and then applied to preparative nonreduced SDS-PAGE (10%; 28). Lanes of the gel were either stained with Coomassie blue or were cut into 4 mm slices, incubated with Na acetate (0.1M; pH 8.3) and octyl-β-glucoside (0.1%) for 15 hr at 4° C. Tubes were then centrifuged (10,000 g) for 5 min, and the supernatant was diluted 1:100 for testing in the PVC Factor IX binding assay. Where indicated, material eluted from the slices of the gel with peak Factor IX binding activity (corresponding to Mr ≈55 kDa) were again subjected to nonreduced SDS-PAGE (10%) and gel elution.

For sequence analysis, ≈55 kDa polypeptide with peak Factor IX binding activity was subjected to SDS-PAGE (10%), transferred to polyvinylidene difluoride (PVDF) membranes, and the ≈55 kDa was subjected to amino terminal sequencing. Proteolytic digestion of protein adsorbed to PVDF pieces was performed by treating strips with polyvinylpyrrolidine solution (0.2%) followed by trypsin in Tris/HCl (pH 8.5), as described (29). The resultant peptide fragments were isolated by reversed-phase HPLC on a $C_8$ column (2.1×5 cm, YMC Inc., Morris Plain, N.J.). Blotted protein samples on PVDF and peptide fragments recovered by HPLC peptide mapping were sequenced using an Applied biosystems Model 470A gas-phase sequencer with an "on-line" PTH amino acid analyzer (30–31).

Coagulation assays were carried out as described previously to assess Factor IXa-VIIIa-dependent of Factor X on endothelium and phospholipid (21,32), Factor Xa-Va-dependent activation of prothrombin on endothelium/phospholipid (33–35), tissue factor/Factor VIIa-dependent activation of Factor X on endothelial cells stimulated with tumor necrosis factor (36), thrombin/thrombomodulin (on bovine ECs)-dependent activation of protein C (37), and activated protein C/protein S-mediated inactivation of Factor Va on ECs (38)(the latter study employed human ECs and human activated protein C, protein S and Factor Va, see below). The prothrombin time (PT) and activated partial thromboplastin times (APTT) were performed by standard methods.

Infusion of calreticulin into mice. Mice were infused via the tail vein with $^{125}$I-calreticulin or $^{125}$I-albumin. Plasma samples were obtained at the indicated times, and clearance data was fit using non-linear regression techniques (SAS Procedure NLIN, Cary N.C.). A biexponential equation (two rate constants) was fit to each of the clearance curves. In addition, an overall clearance rate was calculated from the area under the curve. Immunohistologic studies were performed on the vascular tissue obtained from mice infused with unlabelled calreticulin. At the indicated time after the infusion, animals were sacrificed, organs were removed and fixed by immersion in neutral-buffered formalin (10%), and embedded in paraffin by standard procedures. Sections were rehydrated, blocked in nonfat dry milk (4%), and incubated with goat anti-rabbit calreticulin IgG (40 min at 37° C.). Primary antibody was revealed using a rabbit anti-goat IgG avidin-biotin conjugated system, as per the manufacturer's instructions (Sigma, St. Louis Mo.), with 3-amino-9-ethylcarbazole as chromogen.

To assess deposition of $^{125}$I-calreticulin/$^{125}$I-albumin, the animals were sacrificed, organs removed, rinsed in phosphate-buffered saline and dried overnight (80° C.). Subsequently the weight and radioactivity (cpm) were measured (39). The method of Spady and Dietschy (40) was used to calculate the tissue spaces employing the following formula: tissue space (microliters plasma per gram dry tissue weight) =[cpm in tissue/(grams dry weight×cpm/microliters plasma)]. The cpm per volume plasma was calculated from the average of the cpm in the 0 and 20 min (for albumin) or in the 0 and 10 sec (for calreticulin) samples. To correct for nonspecific tissue trapping of calreticulin, we calculated a tissue space for $^{125}$I-albumin. Therefore the specific tissue space of calreticulin was calculated by subtracting the $^{125}$I-albumin tissue space from the $^{125}$I-calreticulin tissue space (40).

Canine thrombosis and extravascular hemostasis model. In vivo coronary thrombosis was induced with electric current, as described previously (4,41). This model involves instrumentation of the left circumflex coronary artery with a Doppler flow probe to assess coronary blood flow velocity, and placement of a needle electrode intraluminally to initiate thrombus formation. Sampling catheters are present in the left atrium and coronary sinus, and length-segment crystals are placed in the anterior and posterior myocardial walls. Following a 30 min period to allow stabilization of hemodynamic parameters, current was applied (150 µA) to the needle electrode until a 50% increase in blood flow velocity occurs. This has been shown to correlate with a 40–50% decrease in cross-sectional area of the lumen due to thrombus formation at the site of placement of the electrode (41). When the current was turned off, animals received an intracoronary (IC) infusion of either saline (0.5 ml) or the indicated amount of calreticulin in x ml of saline. Blood samples were collected prior to calreticulin infusion, and after the infusion at 1, 5, 10, 15, 30, 60, 90, 120, and 200 min The bleeding tendency at extravascular sites was assessed using a modified incisional bleeding time: a uniform 1 cm deep, 5 cm, long abdominal wall incision was made and a pre-weighed 4×4 inch gauze was inserted for 5 min. The gauze was then removed, reweighed, and the weight of blood loss quantitated, as described previously (4).

Effect of calreticulin on EC production of nitric oxide. Nitric oxide production was studied using the citrulline assay (42), which measures production of $^{14}$C-L-citrulline from by exposing ECs to $^{14}$C-L-arginine.

Results

Figure 1B:
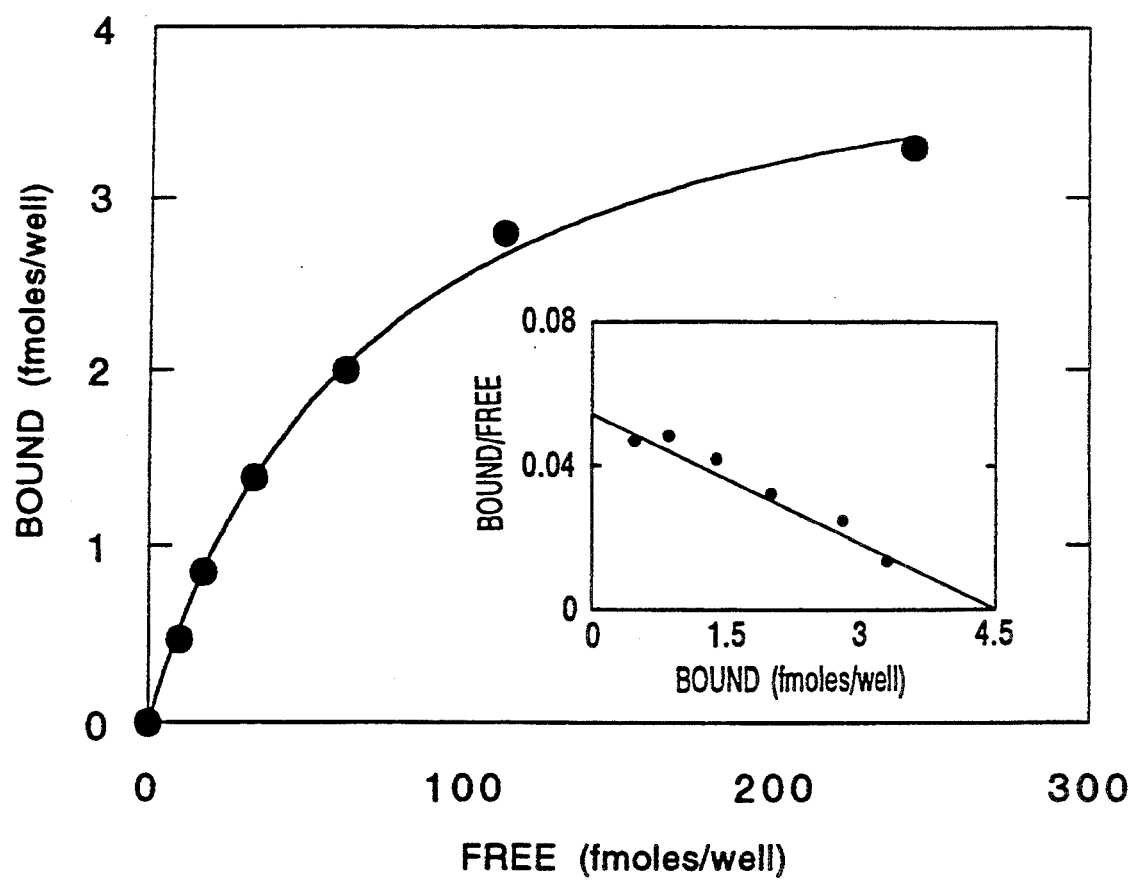
FIG. 1B. Binding of $^{125}$I-Factor IX to lung extract immobilized in PVC wells; dependence on $^{125}$I-Factor IX concentration.
Figure 1C:
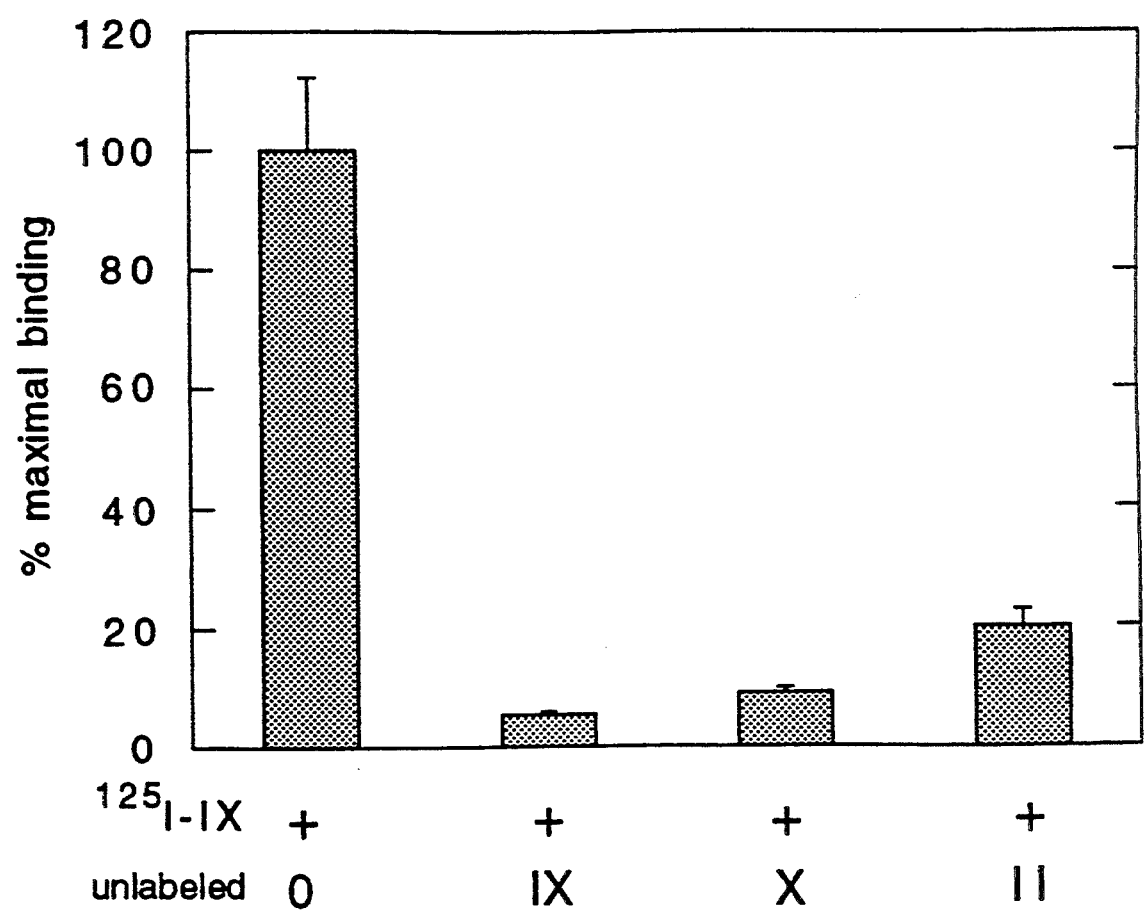
FIG. 1C. Binding of $^{125}$I-Factor IX to lung extract immobilized in PVC wells; competition study with unlabelled Factors IX, X and prothrombin.

Characterization and purification of Factor IX binding activity in bovine lung extracts. To characterize the nature of EC interaction sites for Factor IX, we began with extracts of bovine lung, a rich source of endothelium, as used previously for the purification of EC-associated receptors (44–45). A solid state binding assay was developed in which lung extracts were immobilized on the surface of PVc wells, and subsequent binding of $^{125}$I-Factor IX was examined. Specific $^{125}$I-Factor IX binding (the difference between binding in wells incubated with $^{125}$I-Factor IX alone compared with wells incubated with a 100-fold excess of unlabelled protein) was observed in this assay system; binding was proportional to the concentration of protein in the lung extract incubated with the PVC well, was not observed in control wells coated with albumin, and was blocked by pre-treatment of the extract with trypsin (FIG. 1A). As the concentration of $^{125}$I-Factor IX was varied over a wide range, binding to immobilized lung extract was observed to be dose-dependent with Kd $\approx$1.6 nM (FIG. 1B), close to the affinity of Factor IX for its binding sites on intact ECs and platelets (8–9). However, in contrast to the specific interaction of Factor IX with these cellular surfaces, the binding of Factor IX to lung extract was not selective for this vitamin K-dependent coagulation factor, as competition was also observed with unlabelled Factor X and prothrombin (FIG. 1C).

Figure 2A:
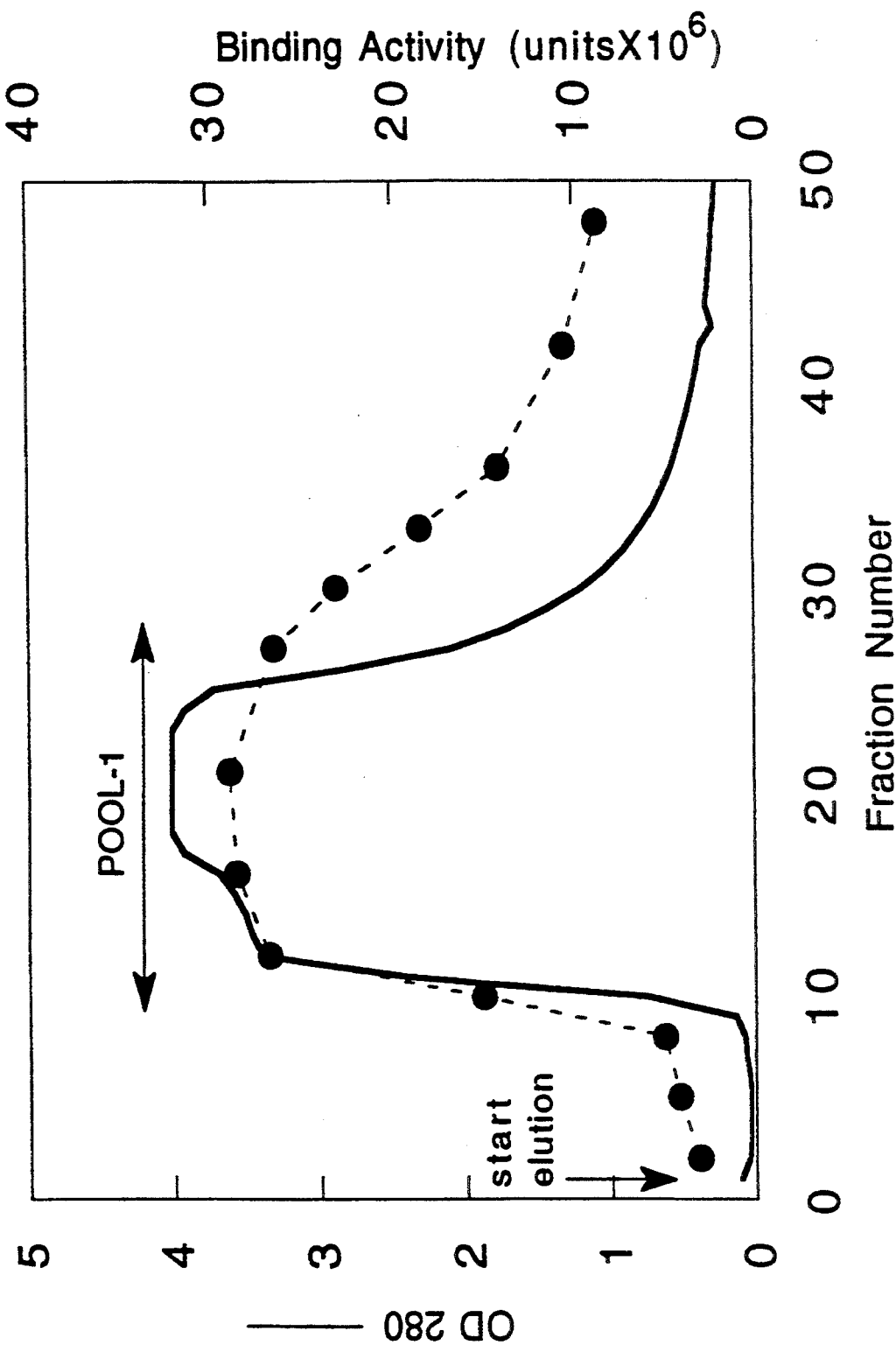
FIG. 2A. Purification of a $\approx 55$ kDa polypeptide from lung extracts based on its ability to bind $^{125}$I-Factor IX in the PVC assay; detergent extract of bovine lung applied to a hydroxylapatite column. OD$_{280}$ (solid line) and binding activity in the PVC assay (broken line) are plotted for each fraction. The active pool of material applied to Mono Q included fractions 10-30, and is indicated.
Figure 2B:
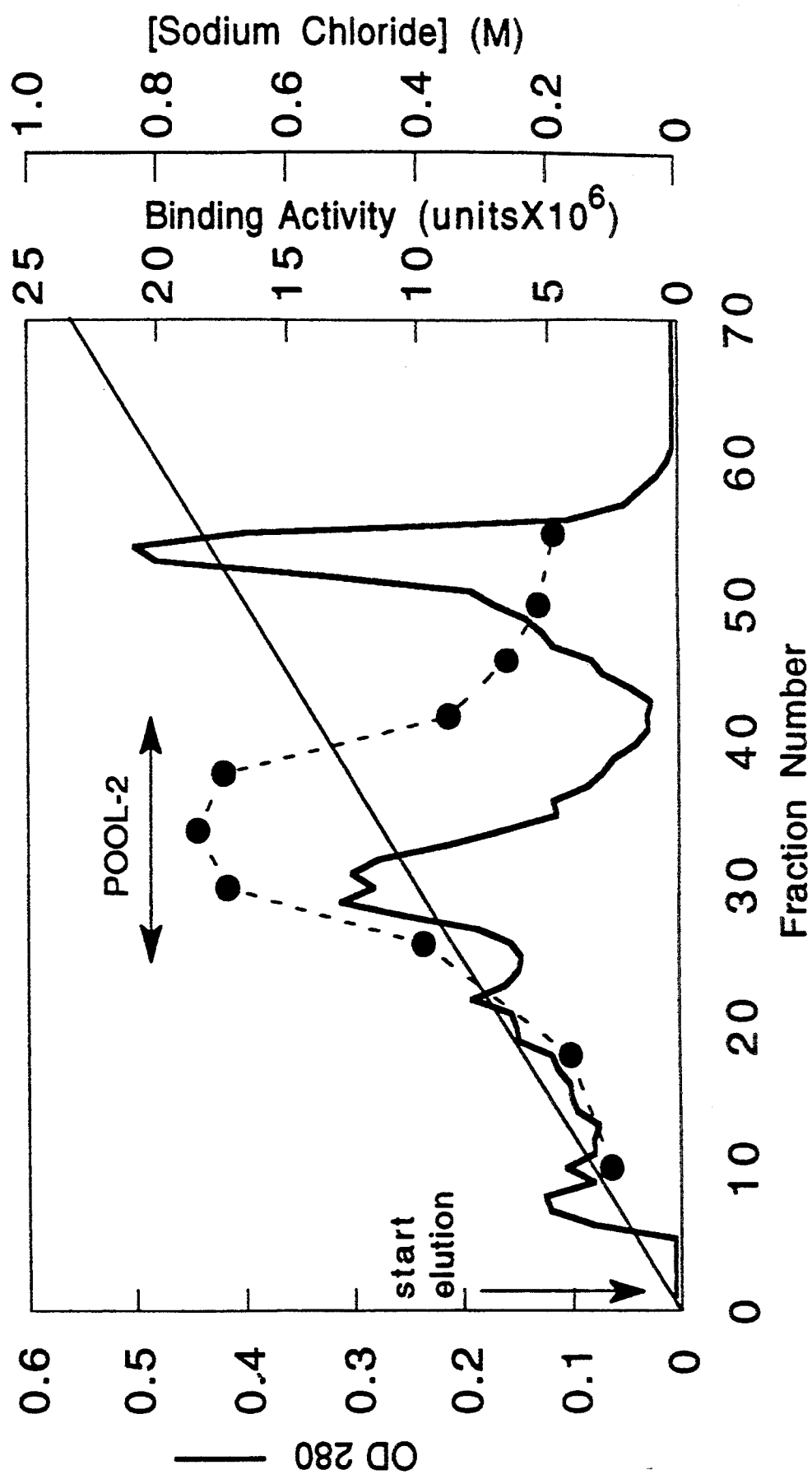
FIG. 2B. Purification of a $\approx 55$ kDa polypeptide from lung extracts based on its ability to bind $^{125}$I-Factor IX in the PVC assay; FPLC Mono Q. The pool with Factor IX binding activity from the hydroxylapatite column was dialyzed and applied to FPLC Mono Q. The pool of fractions from Mono Q subjected to preparative SDS-PAGE is indicated by the bar.
Figure 3:
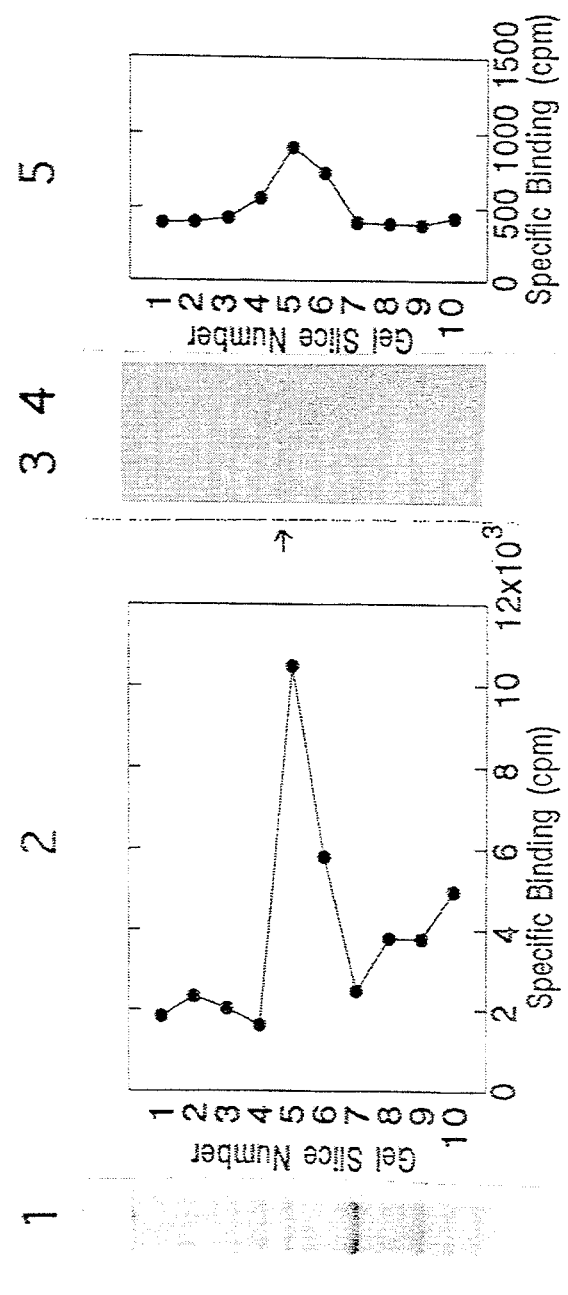
FIG. 3, Lane 1.SDS-PAGE and gel elution of $\approx 55$ kDa polypeptide derived from lung extract which binds Factor IX; nonreduced SDS-PAGE (10%) of the pool from Mono Q with Factor IX binding activity visualized by Coomassie blue staining.

Lung extract was subjected to chromatography on hydroxylapatite, and Factor IX binding activity was recovered with the major protein peak step-eluted with NaPO$_4$ (0.5M)(FIG. 2A). The pool of fractions with Factor IX binding activity was pooled and applied to FPLC Mono Q, and Factor IX binding activity was detected in fractions corresponding to a small protein peak eluted as the column was developed with an ascending salt gradient at $\approx$0.4–0.5M NaCl (FIG. 2B). Fractions with peak Factor IX binding activity were pooled and subjected to reduced SDS-PAGE (FIG. 3, lane 1), and a complex pattern of bands was observed by Coommassie staining. When material in slices of the gel was eluted and tested in the PVC assay, Factor IX binding activity was observed only in fractions which comigrated with a protein band corresponding to Mr $\approx$55 kDa (FIG. 3, panel 2). The latter eluted material was subjected to reduced or non-reduced SDS-PAGE (FIG. 3, lanes 3 and 4, respectively), and in each case a single band, Mr $\approx$55 kDa, was observed. Elution of this protein from the non-reduced gel (FIG. 3, lane 4) demonstrated the presence of Factor IX binding activity in the PVC assay (FIG. 3, panel 5). Based on the sequence of chromatographic and SDS-PAGE/gel elution steps described above, the $\approx$55 kDa polypeptide was purified ≈770-fold from the lung extract to achieve homogeneity (Table 1).

The ≈55 kDa polypeptide band was then subjected to sequencing. A portion of the amino terminal sequence aligned closely with that previously reported for rabbit (46) calreticulin, as well as the human, dog, rat, and pig counterparts (47–49,24)(Table 2). In addition, the band was cleaved with trypsin, fragments were separated on reversed phase HPLC and subjected to sequence analysis (FIG. 4), and found to match those in rabbit calreticulin: #1 residues 262–265; #2 residues 32–36 and 39–43, and #3, residues 306–322 (46).

Figure 6A:
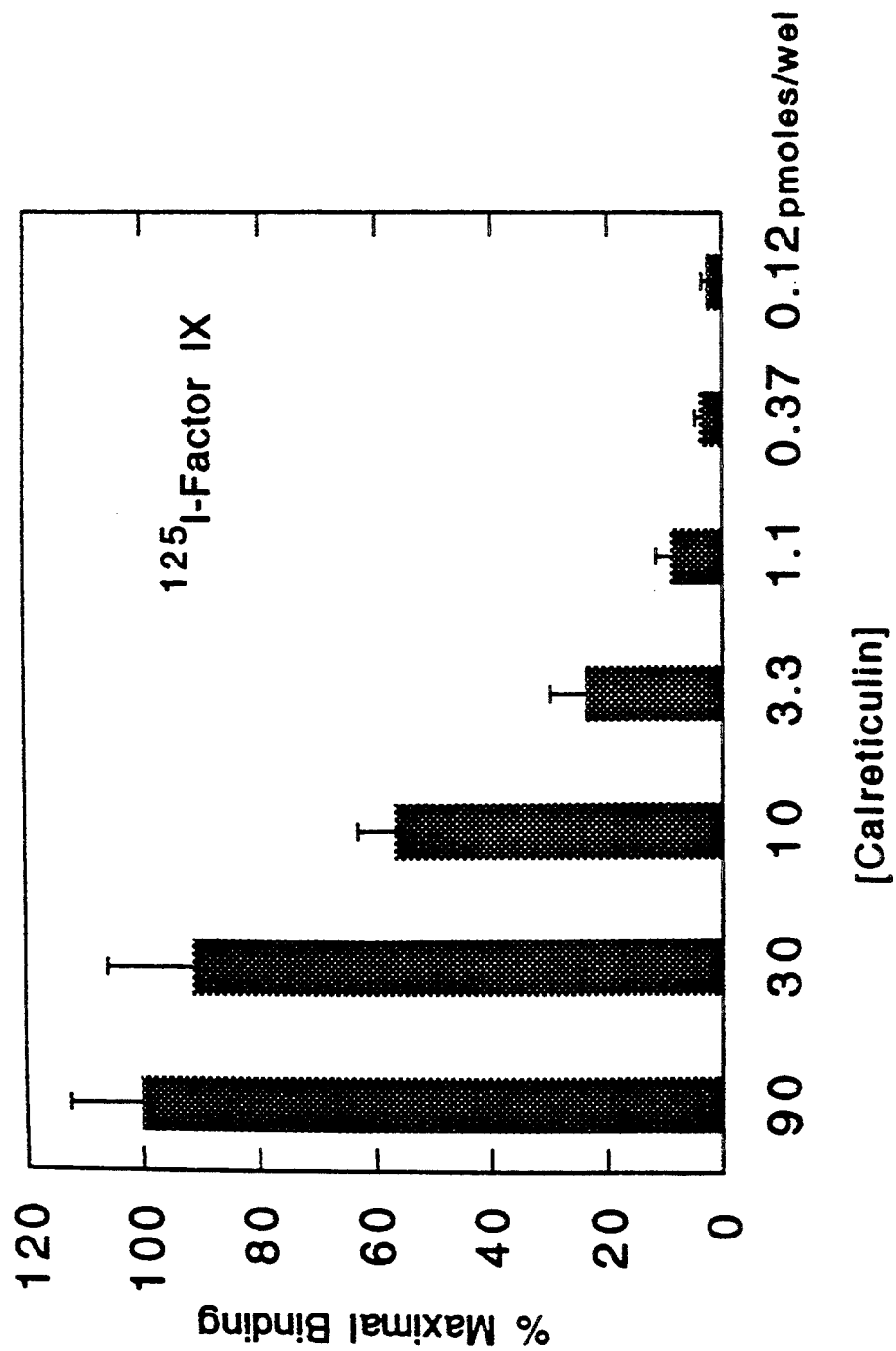
Figure 6B:
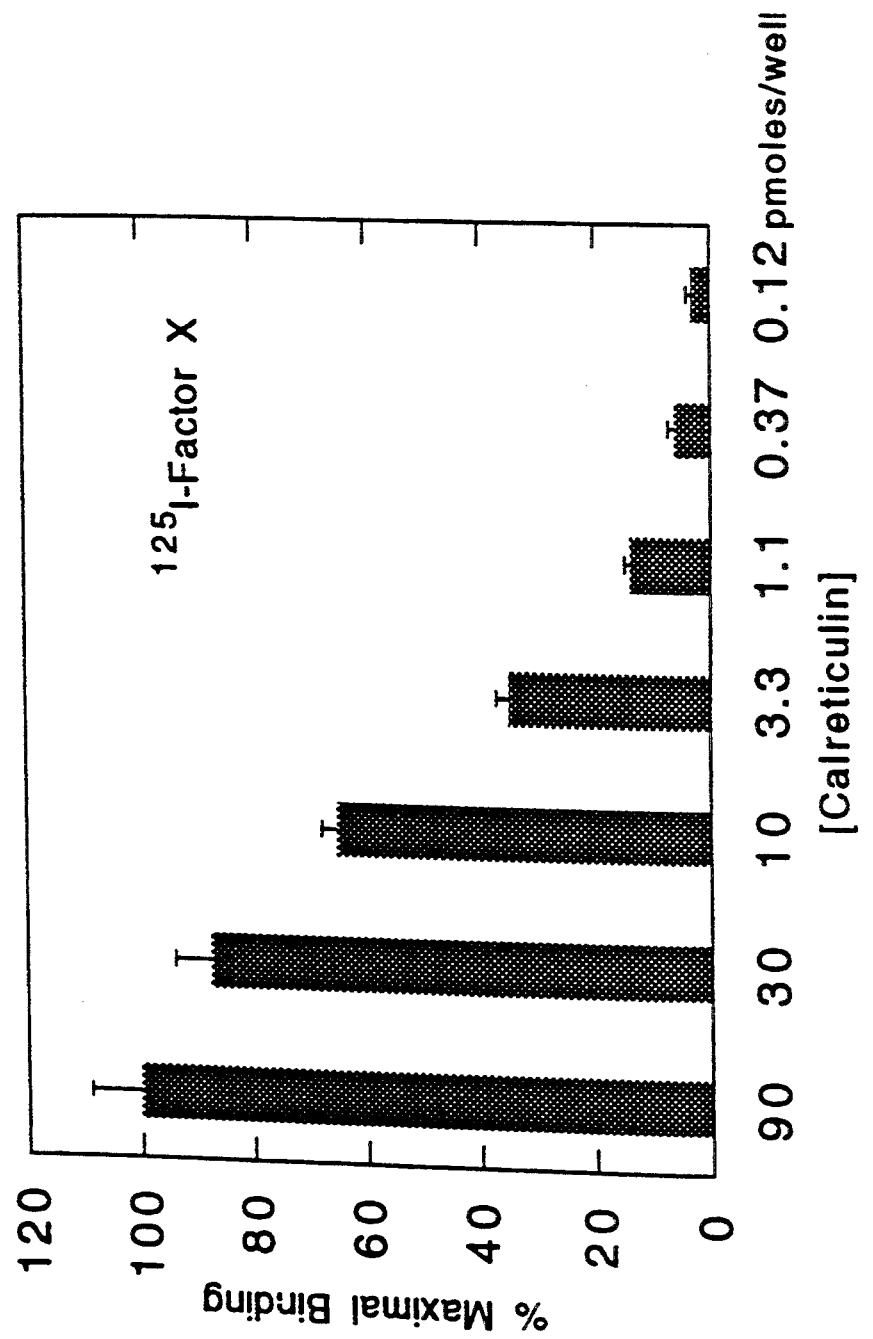
Figure 6D:
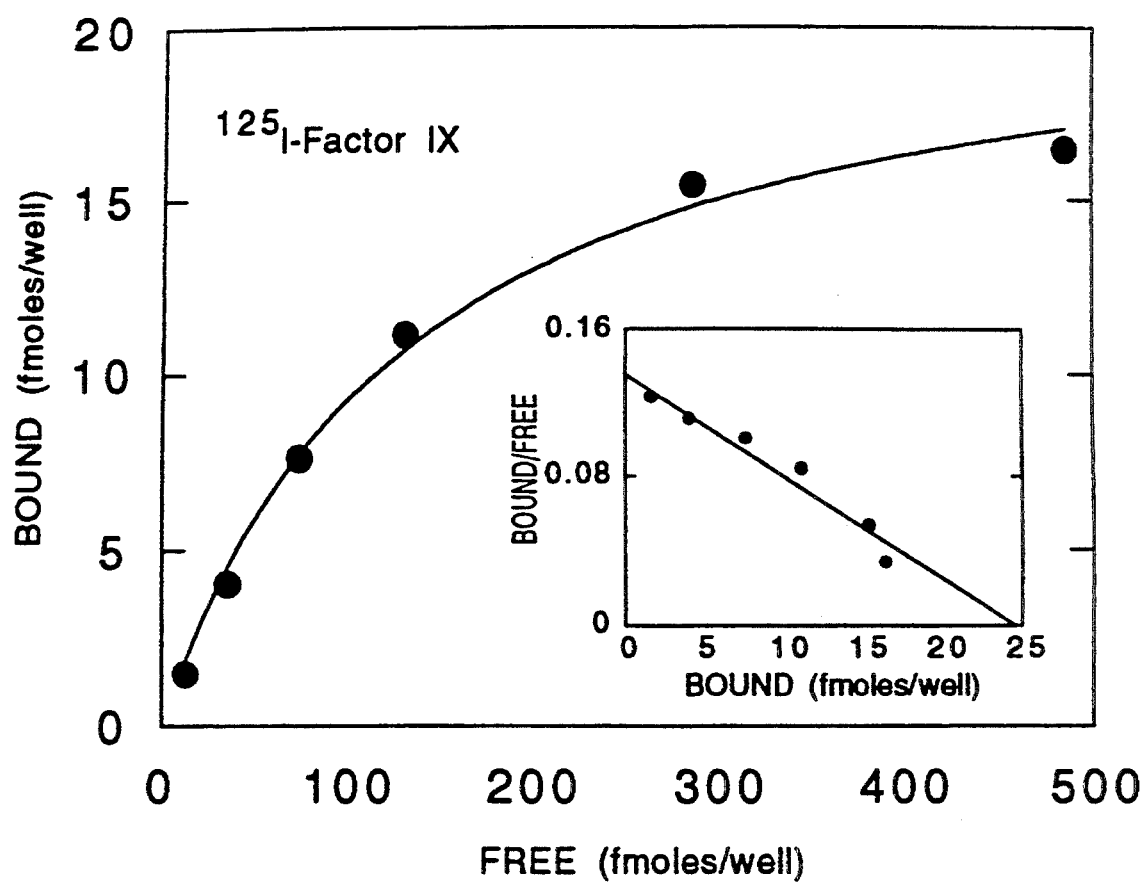
FIG. 6D, 6E, 6F. Binding of Factors IX, X and prothrombin to recombinant calreticulin; dependence on concentration of Factors IX, X and prothrombin. PVC wells were incubated with recombinant calreticulin, excess sites were blocked with blocking buffer, and then a binding assay was performed by adding the indicated concentration of either $^{125}$I-Factor IX (D), $^{125}$I-Factor X (E), or $^{125}$I-prothrombin (F) alone or in the presence of excess of the respective unlabelled protein. Specific binding is plotted versus free/added $^{125}$I-labelled clotting factor (either Factor IX, X or prothrombin). The inset shows Scatchard analysis of the same data.
Figure 6E:
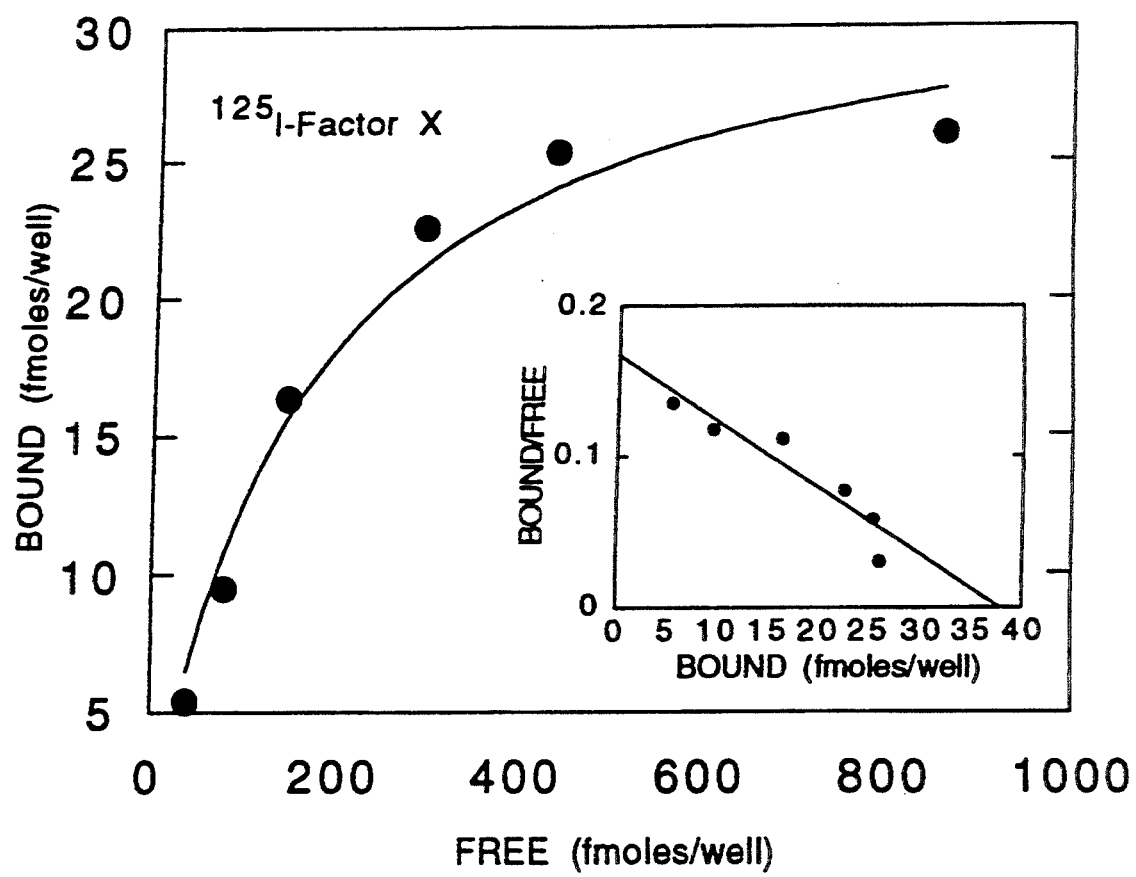
Figure 6F:
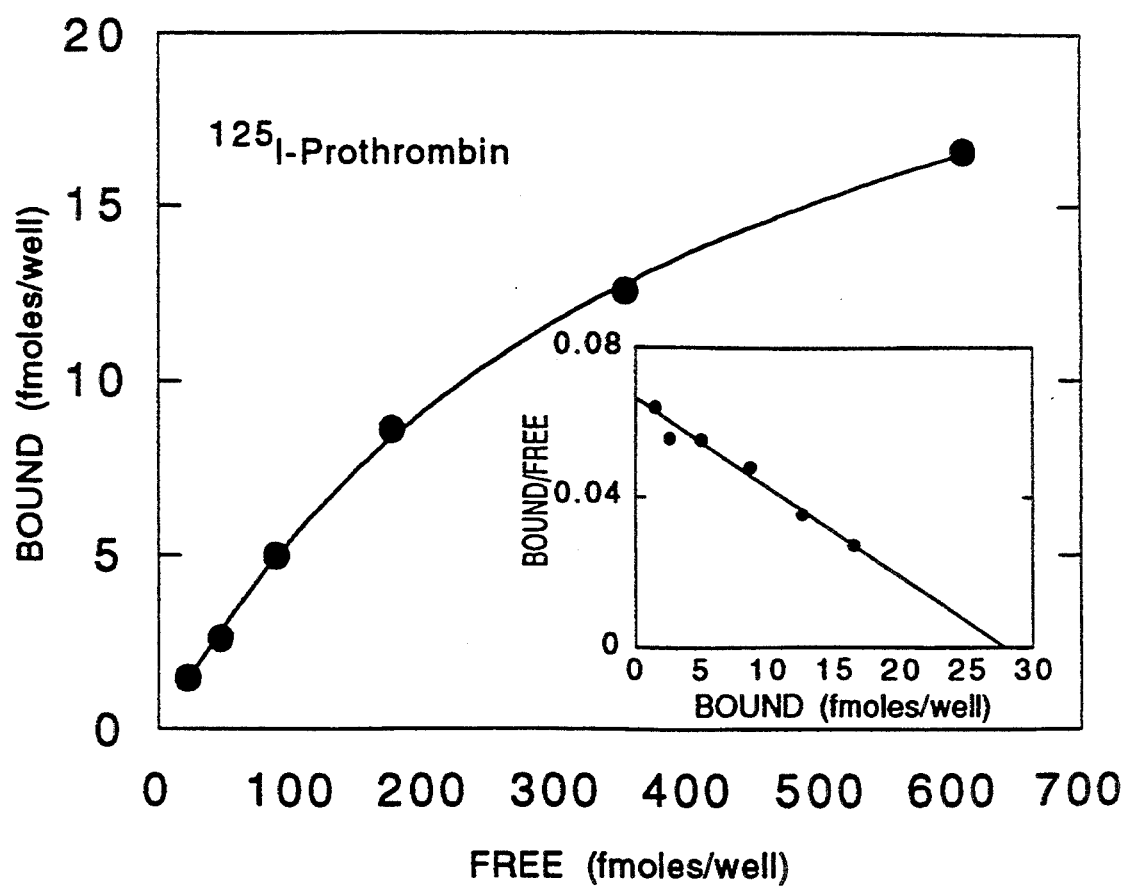

Recombinant calreticulin and its c-terminal domain interact with vitamin K-dependent coagulation factors. These data indicated that the ≈55 kDa polypeptide purified from lung extract was calreticulin. Consistent with this, on reduced and non-reduced SDS-PAGE, purified rabbit calreticulin (bovine calreticulin has not been cloned) and the ≈55 kDa protein from bovine lung extract were shown to comigrate (FIG. 5). Further, recombinant rabbit calreticulin interacted with vitamin K-dependent coagulation proteins similarly to the ≈55 kDa polypeptide in the PVC assay. $^{125}$I-Factor IX binding was observed in wells with adsorbed to calreticulin, and the binding was proportional to the amount of calreticulin incubated with the well (FIG. 6A). Similar binding of $^{125}$I-Factor X and $^{125}$I-prothrombin was observed (FIG. 6B–C, respectively). In each case, interaction of the vitamin K-dependent coagulation factor with calreticulin was dependent on its concentration, demonstrating Kd's of ≈2.7, 3.2, and 8.3 nM, for studies with $^{125}$I-Factors IX, X and prothrombin, respectively (FIGS. 6D,E,F).

Figure 7A:
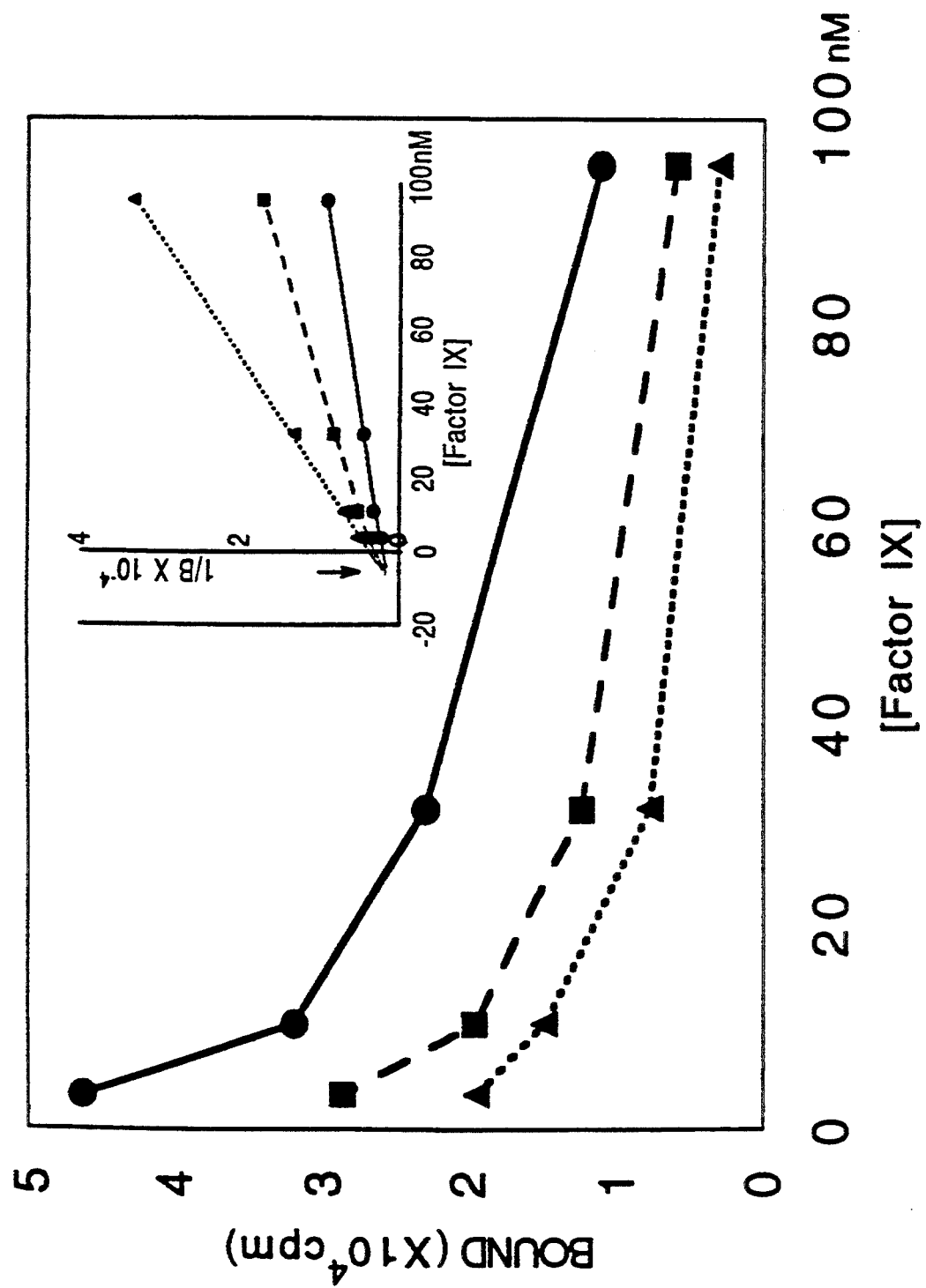
FIG. 7A, 7B, 7C. Competitive binding study: effect of unlabelled Factors IX, X and prothrombin on the binding of $^{125}$I-Factor IX to recombinant calreticulin. Wells were incubated with calreticulin, excess sites in the wells were blocked with albumin-containing buffer, and then a binding assay was performed by adding three different concentrations of $^{125}$I-Factor IX (circle=6 nM; square=3 nM; triangle=1.5 nM) in the presence of the indicated concentrations of either unlabelled Factor IX (A), unlabelled Factor X (B), or unlabelled prothrombin (C). Inset, Dixon plot showing 1/Bound (1/B, fmole$^{-1}$) versus protein added (nM).
Figure 7B:
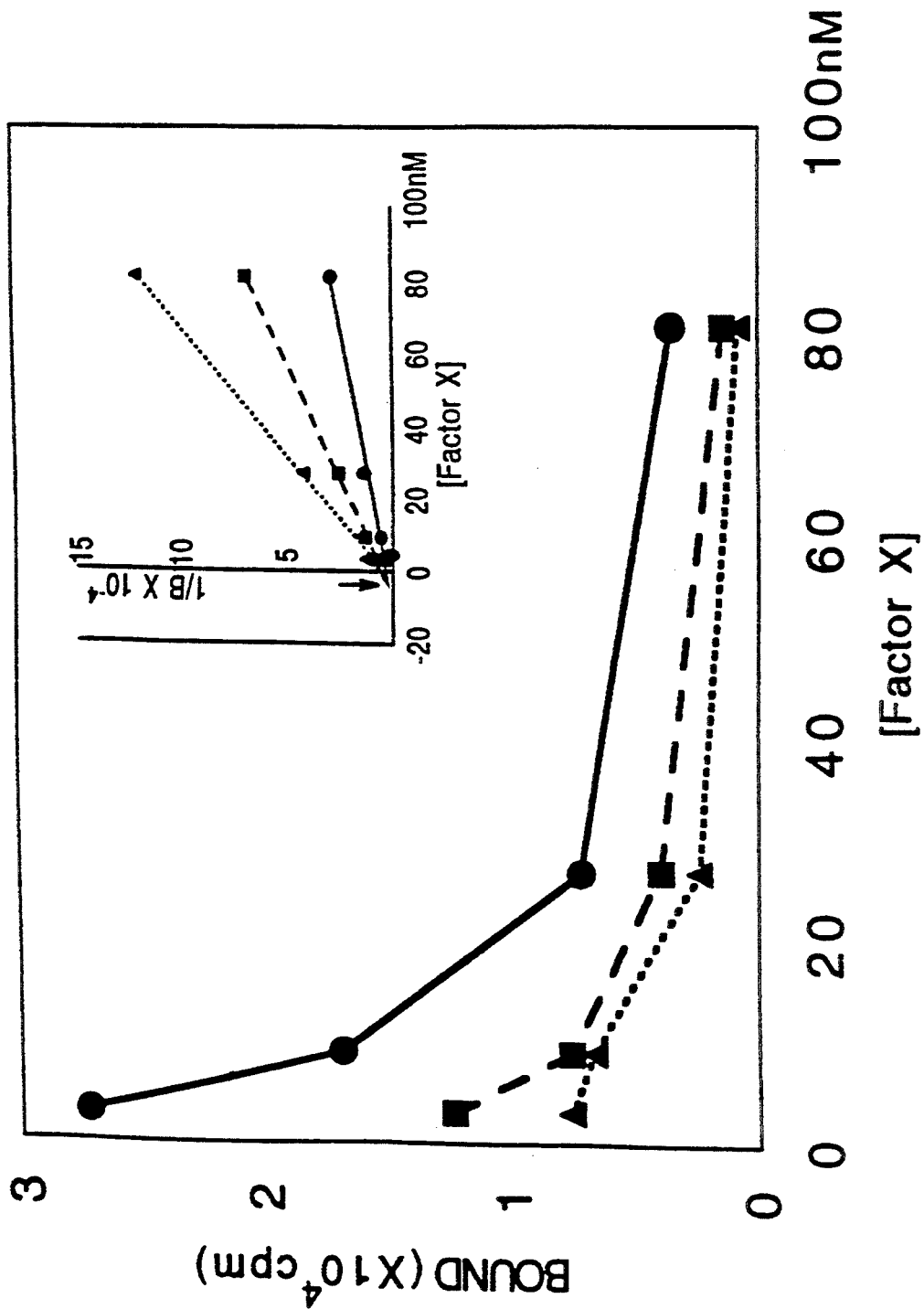
Figure 7C:
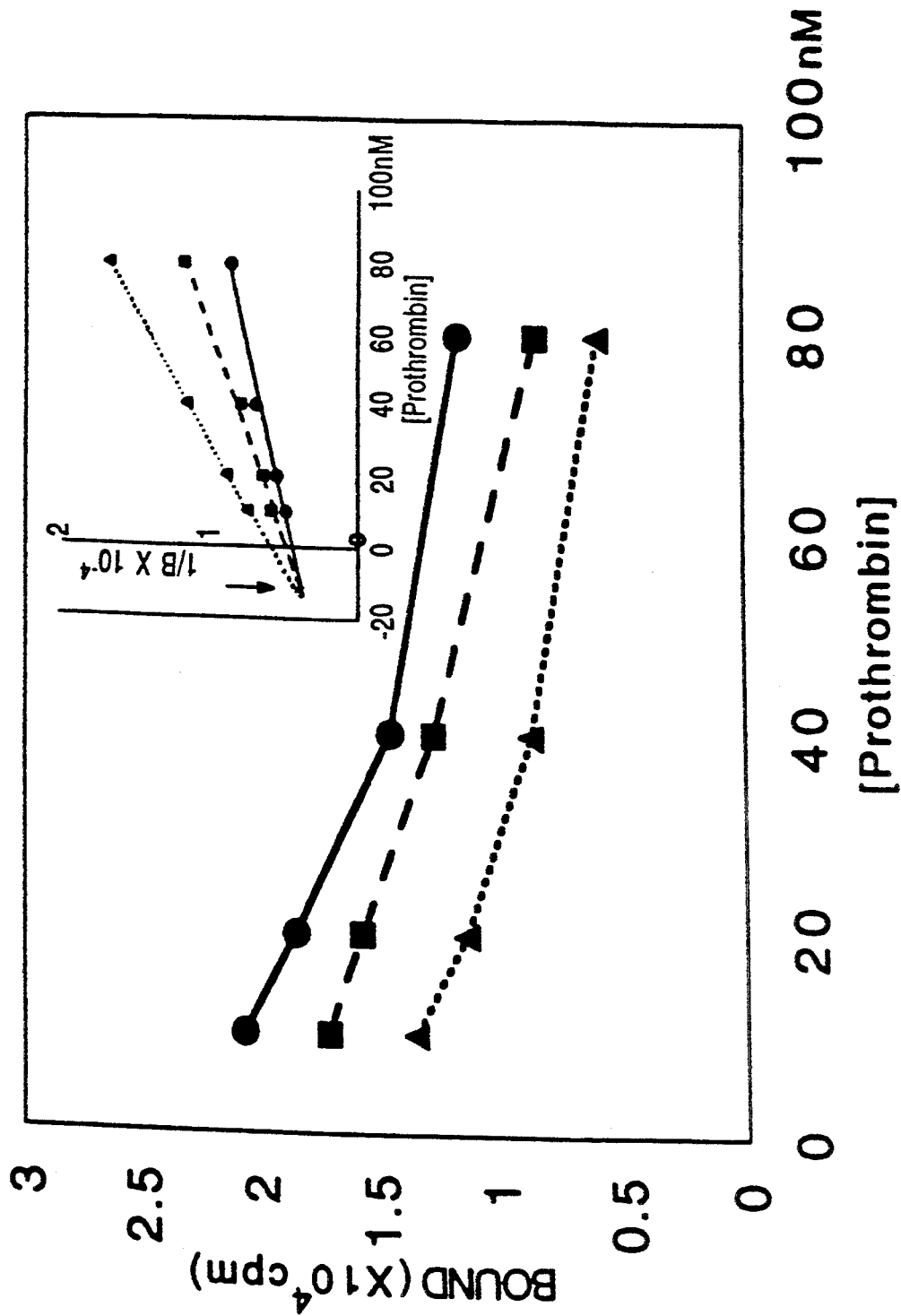

In competition experiments to determine if each of these vitamin K-dependent coagulation factors interacted with identical/overlapping sites on calreticulin. Dose-dependent inhibition of $^{125}$I-Factor IX binding to calreticulin was observed on addition of unlabelled Factors IX, X and prothrombin (FIG. 7A–C, respectively). Although the relationship fits closely to a model of competitive inhibition (26) showing Ki's of ≈6, 5, and 12 nM, for studies -with unlabelled Factors IX, X and prothrombin, respectively (FIG. 7A–C, insets), these values are viewed as approximate. These data suggest that the vitamin K-dependent coagulation factors interacted with similar/overlapping sites on calreticulin.

Figure 8A:
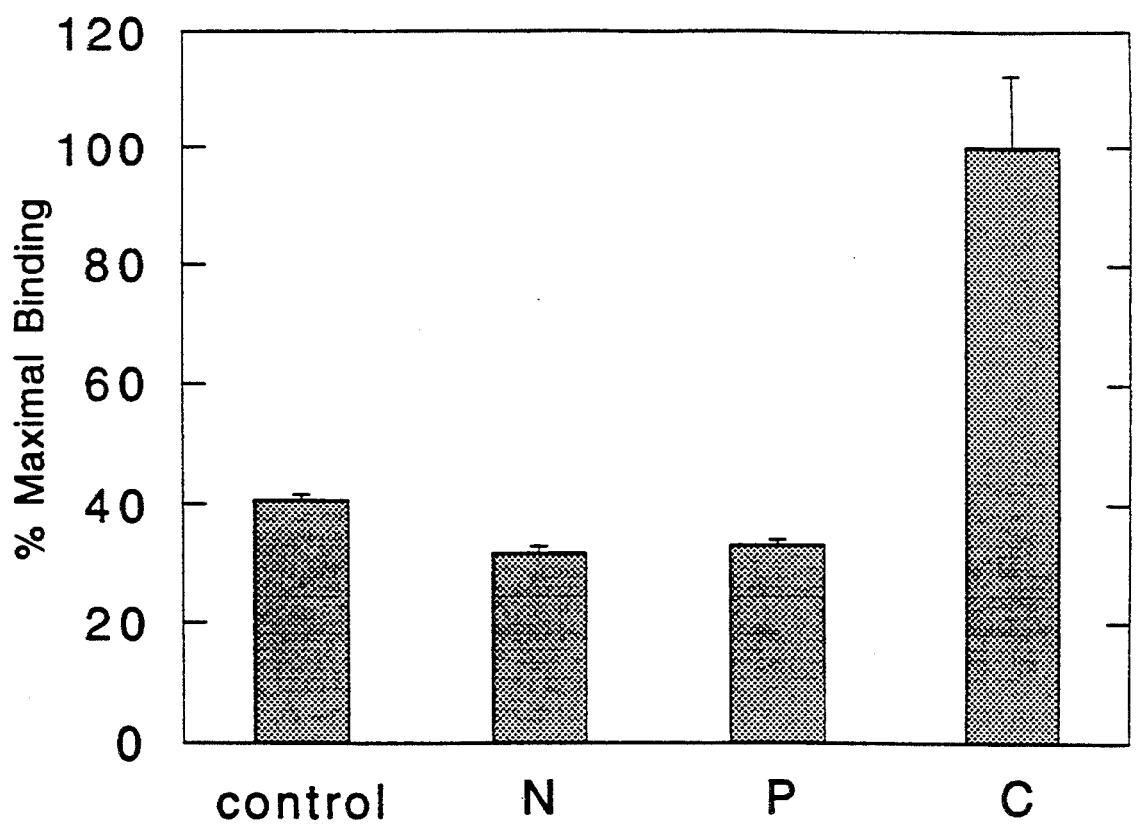
FIG. 8A. Interaction of $^{125}$I-Factor IX with the N-domain, P-domain and C-domain of calreticulin; wells were incubated with the indicated recombinant domain of calreticulin or glutathione-S-transferase control protein, excess sites in the wells were blocked with albumin-containing buffer, and then a binding assay was performed with $^{125}$I-Factor IX alone or in the presence of excess of unlabelled protein. Specific binding is plotted versus the calreticulin domain (N, P or C) used in the assay.
Figure 8B:
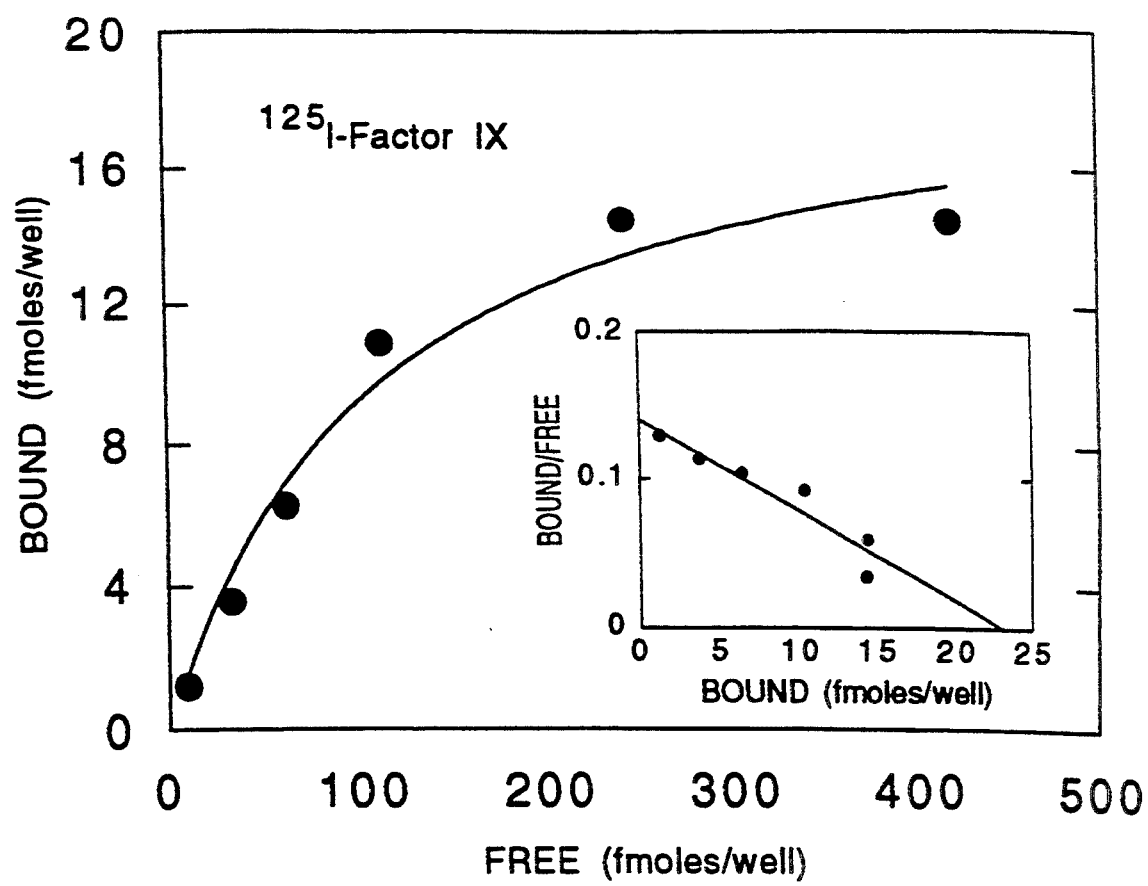
FIG. 8B, 8C, 8D. Interaction of $^{125}$I-Factor IX with the N-domain, P-domain and C-domain of calreticulin; binding of $^{125}$I-Factors IX, X and prothrombin to the C domain of calreticulin; Wells were incubated with C domain, excess sites were blocked with blocking buffer, and then a binding assay was performed with the indicated concentrations of either $^{125}$I-Factor IX (B), $^{125}$I-Factor X (C) or $^{125}$I-prothrombin (D) alone or in the presence of a 30-fold excess of the unlabelled respective protein. Specific binding is plotted versus the concentration of free/added tracer. Parameters of binding were for panel B, Kd=2.2±0.5 nM and N=19.5±1.69 fmoles/well; for panel C, Kd=5.00±0.74 nM and N=39.7±2.72 fmoles/well; and for panel D, Kd=4.79±0.83 nM and N=20.7±1.49 fmoles/well. The inset shows Scatchard analysis of the same data.
Figure 8C:
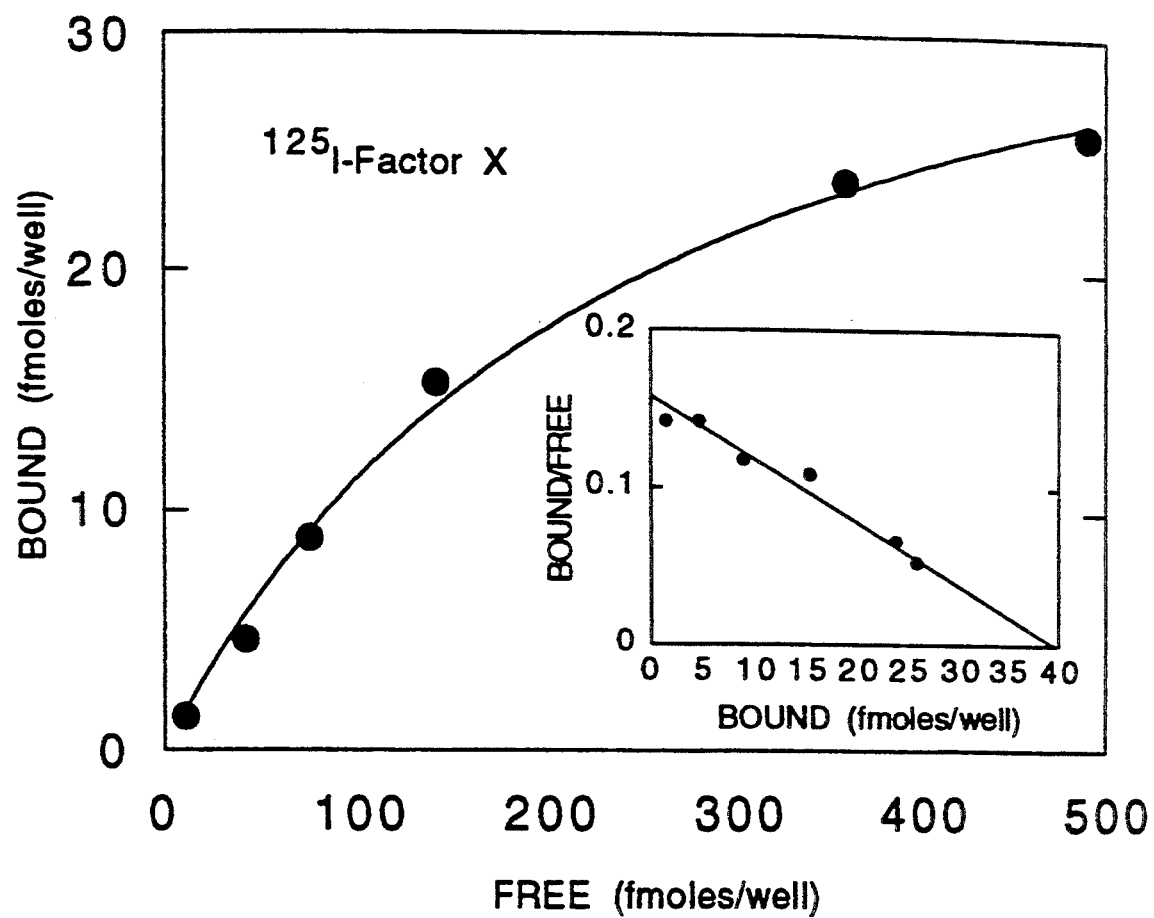
Figure 8D:
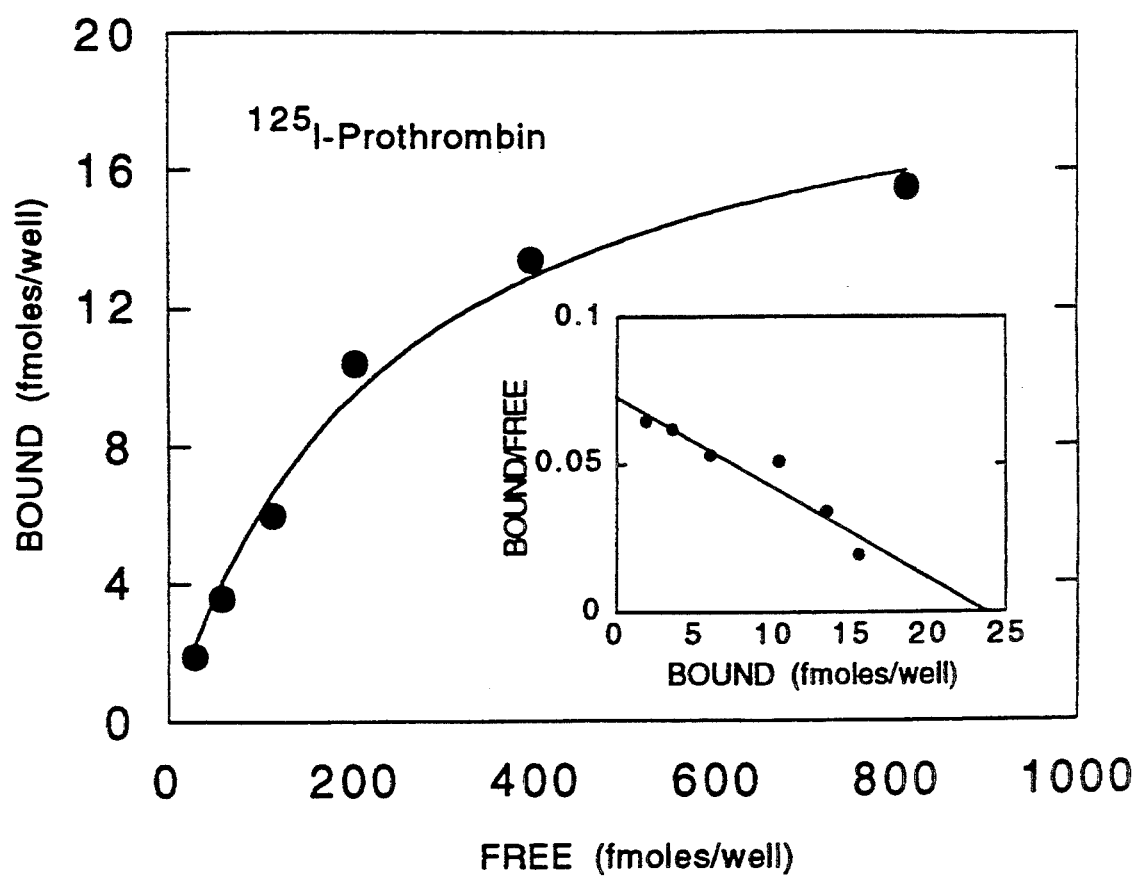

The interaction of calreticulin with $^{125}$I-Factor IX was calcium-dependent, with maximal effect by an added calcium concentration between 2–5 mM (data not shown). Since calreticulin has two calcium binding domains, a high affinity, low capacity site (P-domain) and a low-affinity, high capacity site (C-domain), experiments were performed with each of these domains, as well as amino terminal N-domain (50). Each domain was expressed in *E. coli* using the glutathione S-transferase fusion protein system (24), was purified, and its interaction with vitamin K-dependent coagulation factors was tested in the PVC assay. Only the C-domain bound $^{125}$I-Factor IX, not the P-domain, N-domain or glutathione-S-transferase control protein (FIG. 8A). Studies with vitamin K-dependent coagulation proteins and C-domain indicated that binding was dependent on the concentration of C-domain (data not shown), and on the concentration of radiolabelled clotting factor with Kd's of ≈3.3, 4.8, and 6.0 nM for experiments with $^{125}$I-Factors IX, X, and prothrombin (panels B, C and D, respectively).

In view of the interaction of calreticulin with multiple vitamin K-dependent coagulation factors, we investigated the effect of calreticulin on coagulant reactions involving these proteins. The following reactions were studied: tissue factor/Factor VIIa-mediated activation of Factor X (using matrices prepared from endothelial cells exposed to tumor necrosis factor as the source of tissue factor)(36), Factor IXa-VIIIa-mediated activation of Factor X (using crude cephalin as the phospholipid surface or endothelium), Factor Xa-Va-mediated activation of prothrombin (using cephalin as the phospholipid surface or endothelium), and thrombomodulin-dependent, thrombin-mediated activation of protein C (using intact bovine ECs as the source of thrombomodulin)(37). No inhibition of these reactions was observed over a range of calreticulin concentrations. Furthermore, addition of calreticulin to recalcified human or bovine plasma did not delay clotting initiated with Factor IXa or Factor Xa (employing cephalin as the phospholipid source).

Figure 9A:
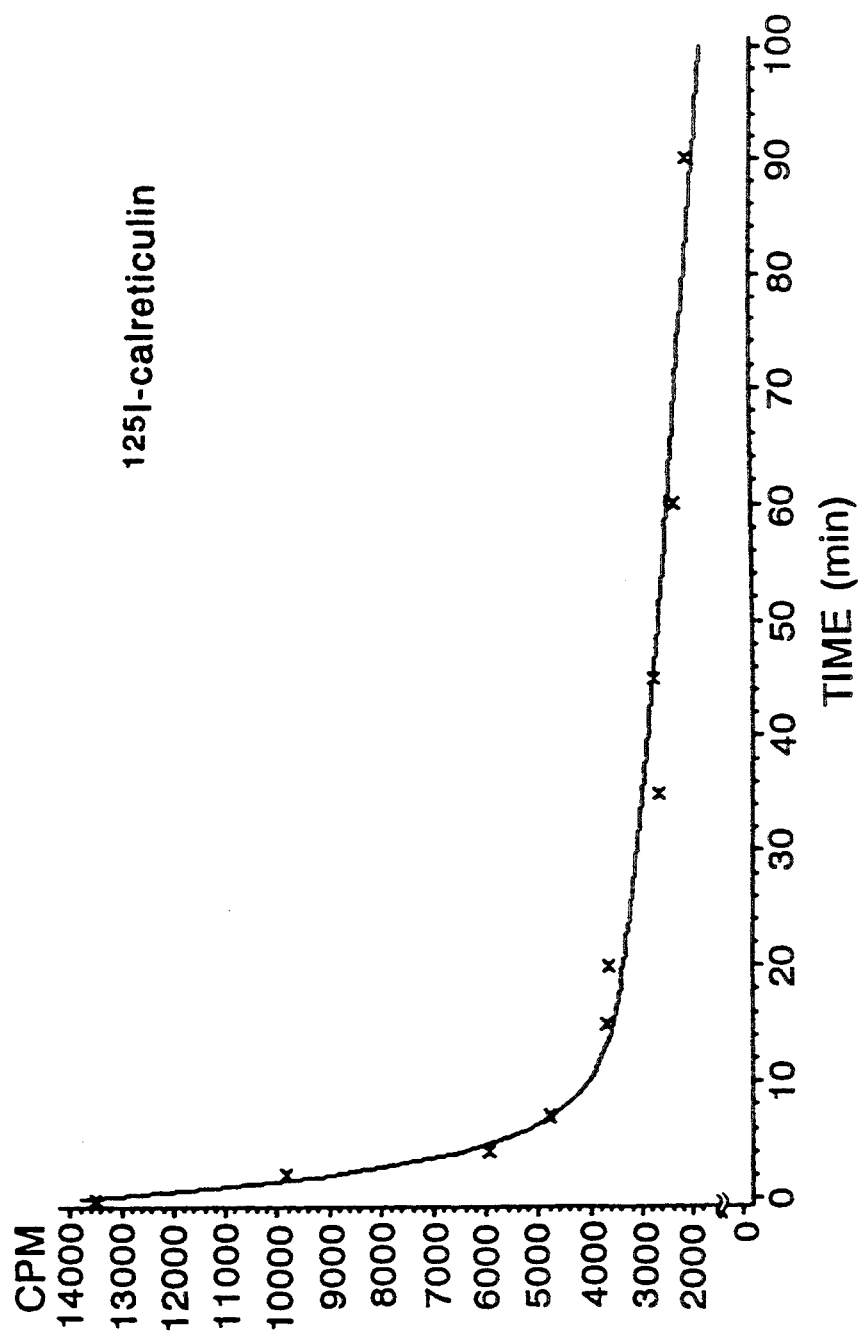
FIG. 9A. Infusion of recombinant rabbit calreticulin into mice; removal of infused $^{125}$I-calreticulin from the plasma. Mice were infused via the tail vein with $^{125}$I-calreticulin, and at the indicated times blood was withdrawn for determination of radioactivity.

Infusion of calreticulin into mice. To further assess cellular interactions of calreticulin, $^{125}$I-calreticulin was infused intravenously into mice. Calreticulin clearance data was best fit by a bi-exponential equation (FIG. 9A). The $t_{\frac{1}{2}}$ for the fast rate constant ranged from 1.3–2.7 min, and the $t_{\frac{1}{2}}$ for the slow rate constant ranged from 91–186 min. The intercept for the fast component ranged from 72–83%, while the slow component ranged from 17–28%. The $t_{\frac{1}{2}}$ for the overall clearance rate ranged from 27–34 min. Studies were also performed with $^{125}$I-albumin (FIG. 9B) in order to compare the results with the calreticulin infusion. Albumin clearance data was best fit by an exponential plus a constant. The $t_{\frac{1}{2}}$ for the rate constant was ≈21 min. However, almost two-thirds of the injected radioactivity was not cleared within the time frame of the experiments (within 90 min). A rapid phase of disappearance from the plasma, complete within ≈10 min, was followed by a slower phase of clearance (FIG. 9A). Thus, the rapid phase of clearance observed with calreticulin was not seen with albumin. The slower rate constant for calreticulin, on the order of 20–30 min, was similar to that seen with albumin, and is likely to represent a different mechanism.

The tissue deposition of $^{125}$I-calreticulin 20 min after its infusion was studied by comparing accumulation of $^{125}$I-calreticulin with $^{125}$I-albumin (39–40). Radiolabel was present in the most vascular organs, with the greatest amount in the lung (FIG. 9C). The trichloroacetic acid precipitability of $^{125}$I-calreticulin present in the plasma or lung was not significantly changed 10 and 60 min after its infusion, suggesting that rapid degradation was not occurring (data not shown). Immunohistochemical studies showed that infused calreticulin (FIG. 9D- panel I), whereas no staining was observed in saline-treated controls (FIG. 9D- panel II) or when anti-rabbit calreticulin IgG was replaced with nonimmune IgG (data not shown).

Figure 10:
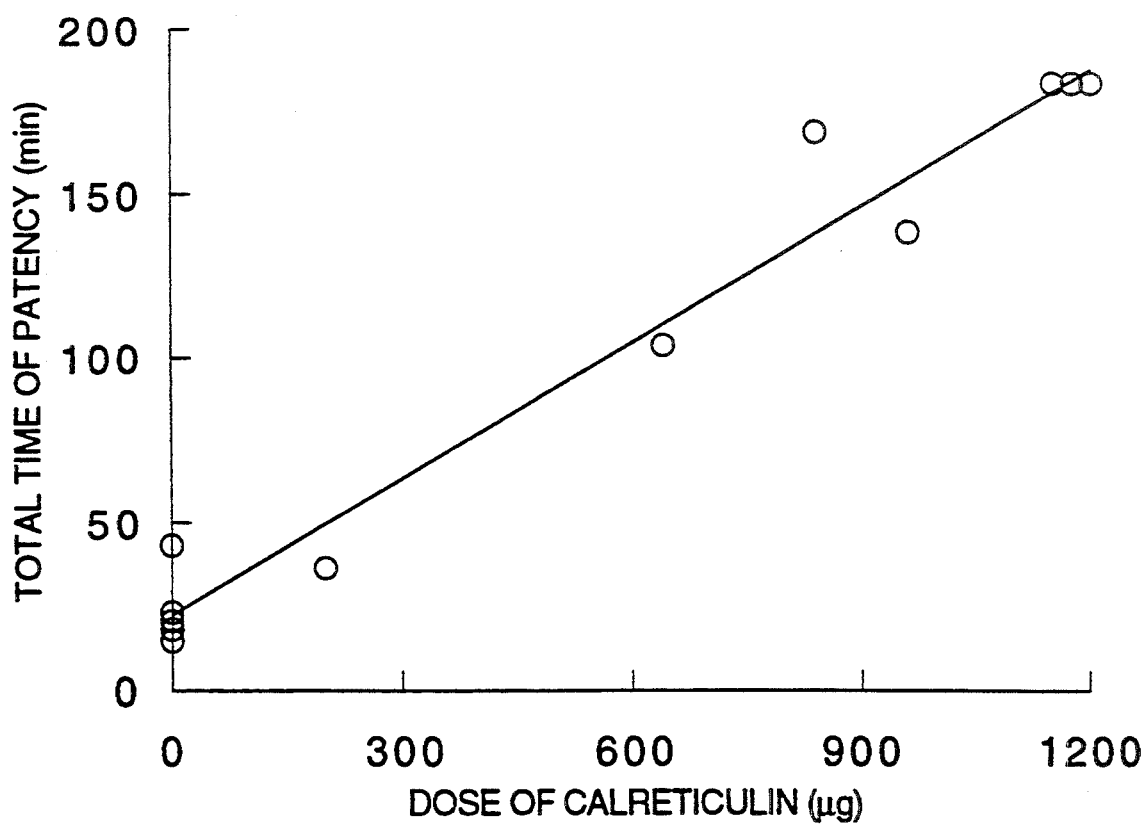
FIG. 10. Effect of calreticulin on coronary thrombosis in a canine model.

Effect of calreticulin on thrombosis and the hemostatic response in a canine model. In view of the association of infused calreticulin with the vessel wall, experiments were performed in a thrombosis model to determine if it could modulate the procoagulant response. Formation of a thrombus was induced by placement of a needle electrode into the left circumflex coronary artery and application of electric current, as described previously (4). When blood flow was diminished by 50%, based on measurements from flow catheters, the current was discontinued and animals received either saline (1 ml) or calreticulin administered into the left circumflex artery (FIG. 10). The weight of animal is about 22–24Kg. All animals treated with saline (N=5) developed occlusive thrombosis with cessation of blood flow within 20–45 min. In contrast, animals receiving calreticulin (N=3) did not develop thrombosis, and the vessel stayed open for the duration of the experiment (180 min). The antithrombotic properties of calreticulin in this model were roughly proportional to the infused dose, with maximal effect at 1.2 mg/animal and steadily diminishing to finally no effect by 200 μg/animal (FIG. 10). Although calreticulin (1.2 mg/animal) blocked thrombus formation, there was no effect on the prothrombin time or activated partial thromboplastin time based on testing serial plasma samples collected from coronary sinus blood at times up to 200 min (data not shown). Furthermore, animals displayed no evidence of a bleeding tendency assessed using a standardized abdominal incision model (4) or by gross inspection of incision/catheter insertion sites.

Figure 11A:
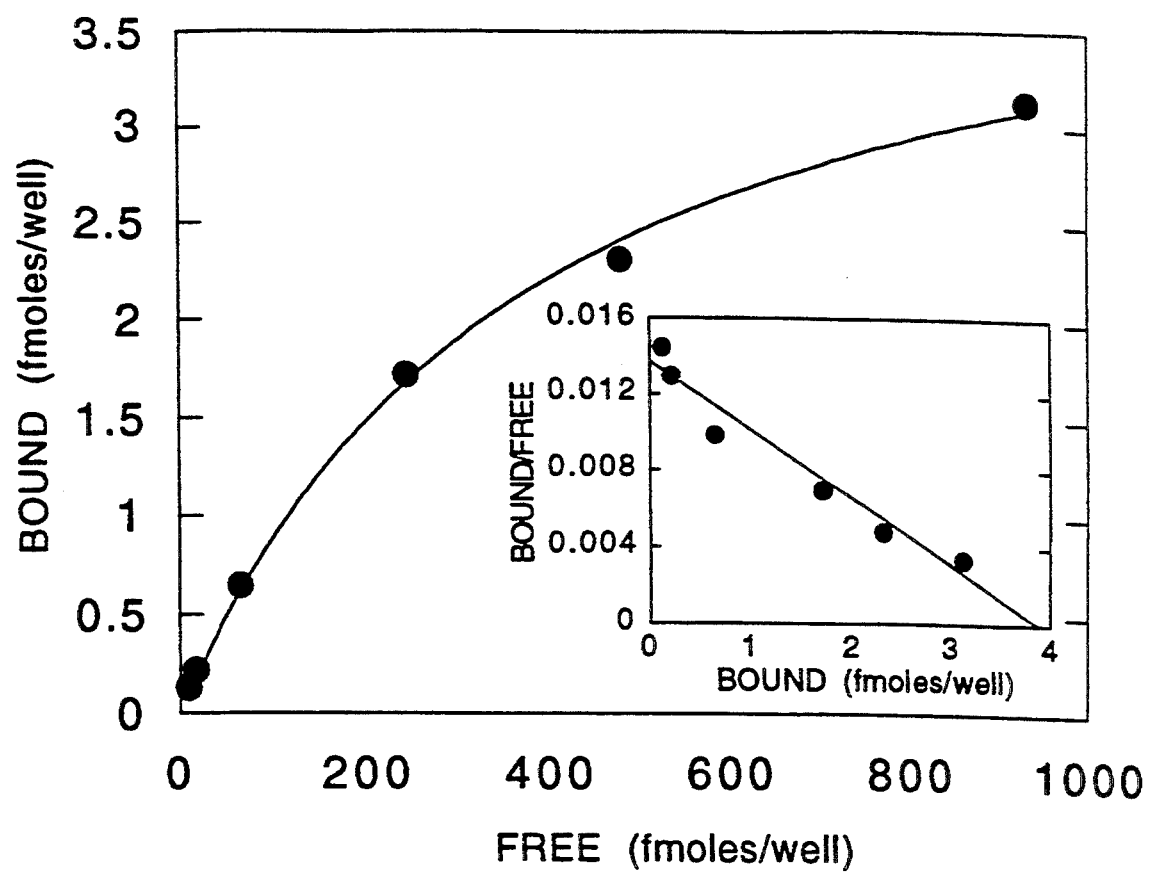
FIG. 11A. Binding of calreticulin to ECs; dose-dependence.
Figure 11B:
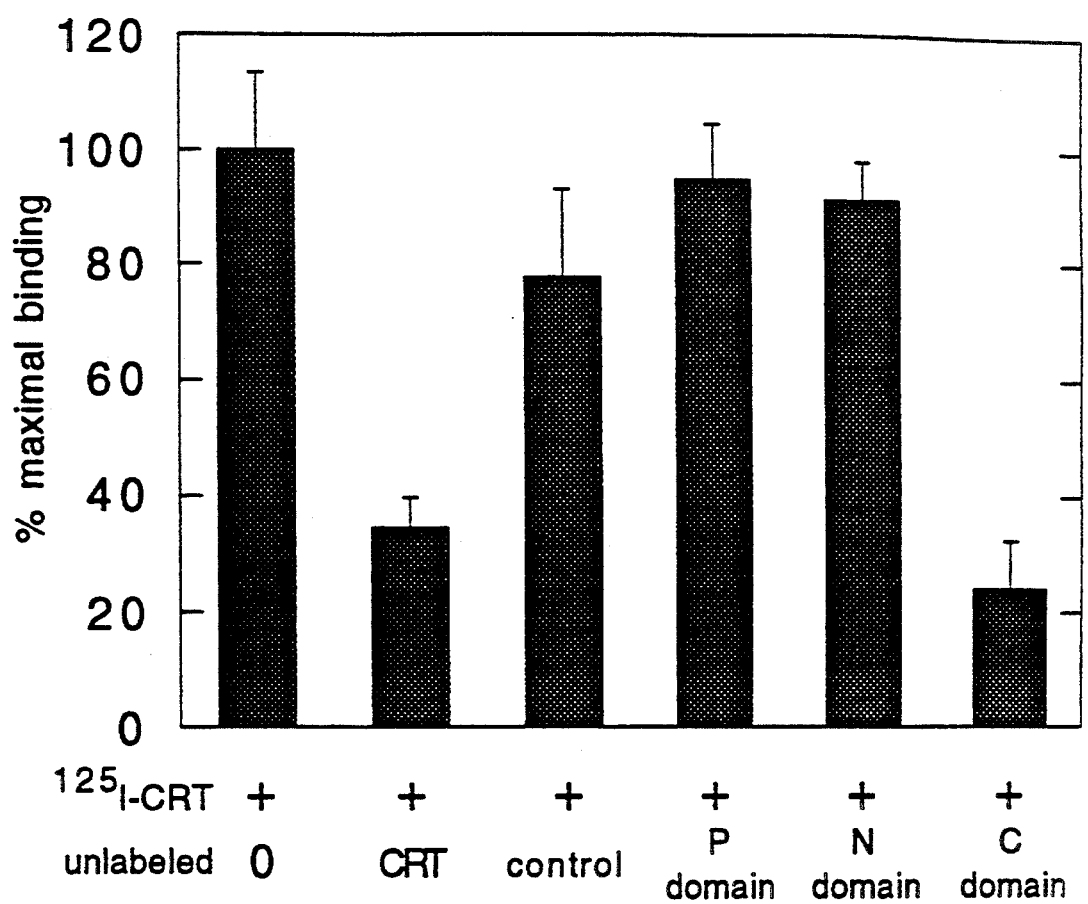
FIG. 11B. Binding of calreticulin to ECs; competitive binding study of $^{125}$I-calreticulin binding to endothelium: effect of unlabelled C-domain.

Interaction of calreticulin with Ecs. These data suggested that calreticulin interacted with endothelium, and thereby could buttress anticoagulant mechanisms on the EC surface. Therefore, binding studies were performed with $^{125}$I-calreticulin and confluent monolayers of bovine aortic endothelial cells (ECs). $^{125}$I-calreticulin bound to ECs in a time-dependent and reversible manner (data not shown), which was proportional to the dose of added radioligand (Kd $\approx$7.4 nM)(FIG. 11A). EC-calreticulin interaction was blocked by unlabelled intact calreticulin and C-domain, but not by the P- or N-domains (FIG. 11B).

These data showing that calreticulin could bind to the vessel surface in vivo, and suggested that such binding might augment natural antithrombotic mechanisms, such as production of nitric oxide. Using the citrulline assay, increased nitric oxide synthase activity (FIG. 12) was evident at 0.5 and 3 hrs after incubation with calreticulin.

Discussion

To understand the nature of the interaction of Factor IX with endothelium a $\approx$55 kDa polypeptide was isolated from lung extracts based on its capacity to bind Factor IX. The $\approx$55 kDa co-migrated on SDS-PAGE with calreticulin, and displayed virtual sequence identity with calreticulin of five different species. Furthermore, recombinant calreticulin bound Factor IX in a manner analogous to the $\approx$55 kDa lung-derived polypeptide. These data indicated that the polypeptide isolated from lung was calreticulin, a previously described intracellular calcium binding protein found in the endoplasmic and sarcomplasmic reticulum (50), but its relationship to the EC binding site was unclear, as indicated by several lines of evidence: (i) the binding of Factor IX to either the $\approx$55 kDa polypeptide or calreticulin was not selective since the interaction with other vitamin K-dependent factors, including Factor X, prothrombin, and protein S (for the latter, data not shown), was very similar and the coagulation proteins cross-competed, whereas binding to the EC surface is selective for Factor IX; (ii) addition of excess unlabelled calreticulin to binding mixtures of $^{125}$I-Factor IX-EC incubation mixtures did not prevent specific binding; and (iii) antibody to human calreticulin did not block the binding of $^{125}$I-Factor IX to human ECs (data not shown). These data suggest that the interaction of Factor IX with the endothelium does not involve calreticulin.

Although the binding of calreticulin to vitamin K-dependent coagulation factors appears to be relatively non-selective with respective to the target clotting factor, it specifically involves the C-domain of calreticulin. The first probable evidence supporting an interaction between calreticulin and vitamin K-dependent coagulation proteins derives from the observation that calreticulin was a persistent contaminant co-purifying with protein Z, requiring preparative electrophoresis to effect a complete separation (51). However, the same authors found that calreticulin was present in apparently normal human plasma (at levels of $\approx$60 ng/ml)(51), despite the presence of an endoplasmic retention sequence and two lysosome targeting signals (50). These data suggest that calreticulin is likely to bind to plasma vitamin K-dependent coagulation proteins under physiologic conditions, although the functional significance of this interaction is unclear, especially in view of our inability to find any affect of calreticulin on the participation of Factor VIIa, Factors IX/IXa, X/Xa, prothrombin, protein C/activated protein C and protein S in coagulation-related reactions.

The results of our in vivo clearance studies suggested that calreticulin was likely to become rapidly associated with the vessel wall. In addition, it was capable of exerting an antithrombotic effect when infused into the coronary vasculature, without altering plasma coagulation parameters or resulting in a bleeding tendency. A recent pilot study with calreticulin administered via a peripheral vein (6 mg) also showed a protective antithrombotic effect in the same canine thrombosis model, without evidence of extravascular bleeding at incision sites or in response to our modified incisional bleeding time (data not shown). These data suggested the possibility that calreticulin might bind to the endothelium and alter its coagulant properties, potentially favoring anticoagulant pathways. Consistent with this concept, calreticulin bound specifically to cultured ECs, and resulted in enhanced release over time of tPA, prostacyclin, and nitric oxide. The well-known antithrombotic efficacy of each of these mediators leads us to propose that although calreticulin stimulates only a 2–4-fold increase in EC elaboration of these agents above the unstimulated baseline, taken together, these could significantly dampen activation of coagulation.

Although the precise mechanism through which calreticulin blocks coagulation in vivo is uncertain, it does not appear to be a direct effect on coagulation proteins or on platelet functions, such as ADP- or thrombin-induced aggregation (data not shown). Rather, calreticulin may stimulate ECs resulting in their production of anticoagulant mediators which prevent effective thrombus formation. If these findings can be extrapolated to a range of thrombosis models, calreticulin may prove to be a novel type of antithrombotic agent.

TABLE 1

Purification of $\approx$55 kDa Polypeptide From Lung Extract+

| Step | Protein mg | Activity units* ×10$^9$ | Specific activity U/mg × 10$^6$ | Yield % | Purf. (for each step) |
|---|---|---|---|---|---|
| lung extract | 2460 | 3.6 | 1.5 | — | 1 |
| HA# | 147 | 2.3 | 22 | 6 | 15 |
| Mono S | 14 | 2.1 | 150 | 9.5 | 6.5 |

TABLE 1-continued

Purification of ≈55 kDa Polypeptide From Lung Extract+

| Step | Protein mg | Activity units* ×10⁹ | Specific activity U/mg × 10⁶ | Yield % | Purf. (for each step) |
|---|---|---|---|---|---|
| SDS-PAGE | 0.3 | 0.345 | 1150 | 2.1 | 8 |

Purf. is an abbreviation for Purification.
*Units are defined arbitrarily; Factor IX binding activity is defined as the product of specifically bound $^{125}$I-Factor IX in the PVC assay x dilution factor of the sample corrected to a sample size of 1 ml.
HA = hydroxylapatite
+ = The starting material was 30 grams of bovine lung acetone powder, and the amount indicated in the top line (lung extract) is that which remained after solubilization in detergent-containing buffer and centrifugation to remove insoluble material (termed lung extract).

TABLE 2

Amino-Terminal Sequence Analysis Of ≈55 kDa Polypeptide From Lung Extract, And Comparison With Sequence Of Calreticulin (CRT)*

| | |
|---|---|
| 55[1] | SEQ ID NO: 1 |
| human[2] CRT | SEQ ID NO: 2 |
| dog[3] CRT | SEQ ID NO: 3 |
| rabbit[4] CRT | SEQ ID NO: 4 |
| rat[5] CRT | SEQ ID NO: 5 |
| pig[6] CRT | SEQ ID NO: 6 |

*Mismatches of the 55 kDa sequence with the indicated sequence are designated by lower case letters.
[1] = Sequence derived from amino terminal sequence analysis of the ≈55 kDa polypeptide purified from bovine lung as described in the text.
[2] = Sequence derived from human calreticulin (47)
[3] = Sequence derived from dog calreticulin (48)
[4] = Sequence derived from rabbit calreticulin (46)
[5] = Sequence derived from rat calreticulin (49)
[6] = Sequence derived from pig calreticulin (26)

Figure Legends

FIG. 1. Binding of $^{125}$I-Factor IX to lung extract immobilized in PVC wells. A. Dependence on extract concentration. PVC wells were incubated with dilutions of lung extract (protein concentration as indicated) for 15 hr at 4° C., additional sites on wells were blocked by exposure to blocking buffer, and then a binding assay was performed by addition of $^{125}$I-Factor IX alone (6.3 nM; total binding) or in the presence of a 100-fold molar excess of unlabelled Factor IX (nonspecific binding) for 2 hr at 4° C.. Wells were then washed, bound $^{125}$I-Factor IX was eluted by exposure to EDTA-containing buffer, and specific binding (total-nonspecific binding) was determined (mean±SEM of triplicate determinations). B. Dependence on $^{125}$I-Factor IX concentration. The experiment was performed as in (A) above, except that the concentration of lung extract was fixed (4 μg/ml), and the concentration of $^{125}$I-Factor IX was varied as indicated. Specific binding is plotting versus the concentration of $^{125}$I-Factor IX added to the wells, and the inset shows Scatchard analysis of the same data. Parameters of binding were: Kd=1.4±0.13 nM and N=4.32±0.17 fmoles/well. C. Competition study with unlabelled Factors IX, X and prothrombin. Lung extract (4 μg/ml) was adsorbed to PVC wells as above, excess sites on the wells were blocked with albumin, and then a binding assay was performed by adding $^{125}$I-Factor IX alone (6.3 nM) or in the presence of a 100-fold molar excess of unlabelled Factors IX, X or prothrombin (II) for 2 hr at 4° C. Unbound tracer was removed by washing, bound $^{125}$I-Factor IX was eluted by exposure to EDTA-containing buffer, and binding (mean±SEM of triplicate determinations) is shown.

FIG. 2. Purification of a ≈55 kDa polypeptide from lung extracts based on its ability to bind $^{125}$I-Factor IX in the PVC assay. Panel A, detergent extract of bovine lung (30 g) was applied to a hydroxylapatite column, the column was washed in equilibration buffer, followed by 1M NaCl, and finally step-eluted with NaPO₄ (0.5M, pH 7.4; the arrow indicates when step-elution was begun). OD$_{280}$ (solid line) and binding activity in the PVC assay (broken line)(assayed at a 1:100 dilution with $^{125}$I-Factor at 6.3 nM) are plotted for each fraction. One binding unit is defined as one count/minute of specific binding of $^{125}$I-Factor IX in the PVC assay/milliliter of sample applied to a PVC plate at a 1:1 dilution. The active pool of material applied to Mono Q included fractions 10–30, and is indicated. Panel B, FPLC Mono Q. The pool with Factor IX binding activity from the hydroxylapatite column was dialyzed and applied to FPLC Mono Q. The column was washed with equilibration buffer and eluted with an ascending salt gradient (50 mM to 1M). OD$_{280}$, salt concentration of the gradient, and binding units in the PVC assay are plotted for each fraction. The pool of fractions from Mono Q subjected to preparative SDS-PAGE is indicated by the bar.

FIG. 3. SDS-PAGE and gel elution of ≈55 kDa polypeptide derived from lung extract which binds Factor IX. Lane 1, nonreduced SDS-PAGE (10%) of the pool from Mono Q with Factor IX binding activity visualized by Coomassie blue staining. Lane 2, activity profile of material eluted from the indicated slice in lane A. A nonstained lane on the gel otherwise identical to lane A was sliced (≈4 mm pieces), subjected to elution as described in the text, and used to coat PVC wells for a binding assay with $^{125}$I-Factor IX alone (6.3 nM) or in the presence of an 100-fold excess of unlabelled Factor IX. Factor IX binding activity is seen to be maximal in the slices (#5–6) corresponding to ≈55 kDa. Data are expressed as counts/min bound per sample of extract. Lanes 3 and 4, the material eluted from slices #5–6 in lane 2 was subjected to nonreduced (lane 3) or reduced (lane 4) SDS-PAGE (10%), and material on the gel was visualized by silver staining. Lane 4, activity profile of the material in lane 3. The material eluted from slices #5–6 in lane 2 was subjected to nonreduced SDS-PAGE (10%) and again the gel was sliced and proteins eluted. The eluted material was test in the PVC assay for its ability to bind $^{125}$I-Factor IX. Details of methods are described in the text, and for activity assays (lanes 2 and 5), the mean of duplicate determinations is shown. Apparent molecular weights, shown by the arrows, were interpolated from semilogarithmic plots based on the migration of standard proteins run simultaneously (phosphorylase B, 90 kDa; bovine serum albumin, 68 kDa; ovalbumin, 46 kDa; carbonic anhydrase, 30 kDa; trypsin inhibitor, 20 kDa; lysozyme, 14 kDa).

Figure 4:
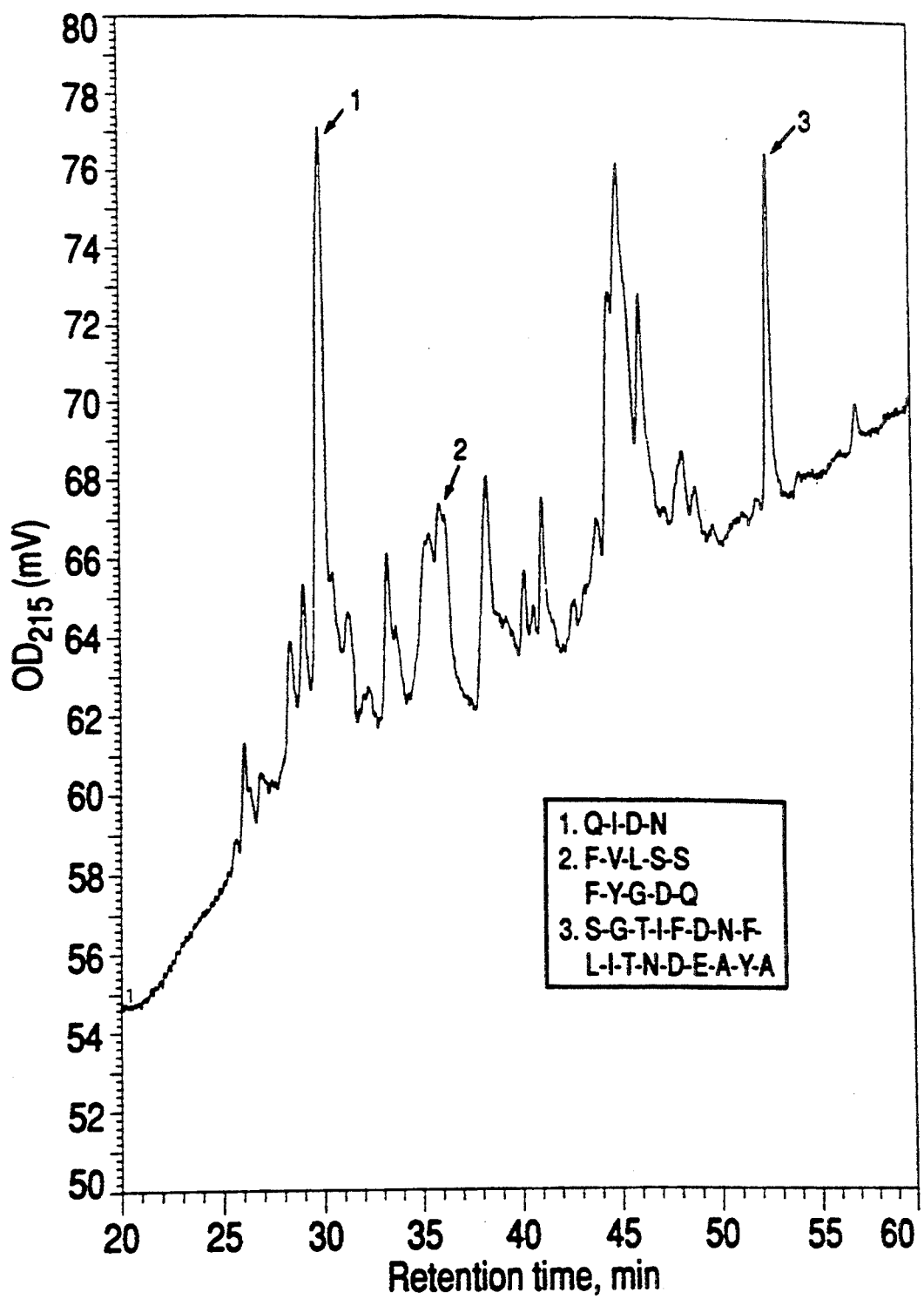
FIG. 4. HPLC reversed-phase chromatography of tryptic digest and protein sequence of fragments (inset) from $\approx 55$ kDa polypeptide isolated by hydroxylapatite and FPLC Mono Q, followed by gel elution.

FIG. 4. HPLC reversed-phase chromatography of tryptic digest and protein sequence of fragments (inset) from ≈55 kDa polypeptide isolated by hydroxylapatite and FPLC Mono Q, followed by gel elution. Details of methods are described in the text. Amino acids in the sequences in the inset are designated by: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Set; T, Thr, V, Val; W, Trp; and Y, Tyr. X is an amino acid residue not identified at that position. Sequence number 1 in the insert is SEQ ID NO:7. Sequence number 2 in the insert is SEQ ID NO:8. Sequence number 3 in the insert is SEQ ID NO:9.

FIG. 5. SDS-PAGE of ≈55 kDa polypeptide and purified, recombinant rabbit calreticulin. The ≈55 kda polypeptide purified from bovine lung extract (1

μg/lane; lanes 1 and 3) or purified recombinant rabbit calreticulin prepared in E. coli (1 μg/lane; lanes 2 and 4) was subjected to nonreduced (lanes 1-2) or reduced (lanes 3-4) SDS-PAGE (10%). Gels were stained with Coomassie blue. Migration of molecular weight markers is indicated by arrows (numbers indicate molecular masses in kDa).

FIG. 6. Binding of Factors IX, X and prothrombin to recombinant calreticulin. A-C. Dependence on calreticulin concentration. PVC wells were incubated with the indicated concentration of recombinant calreticulin, excess sites were blocked with albumin-containing buffer, and then a binding assay was performed by adding either $^{125}$I-Factor IX (6.3 nM; A), $^{125}$I-Factor X (6.0 nM; B) or $^{125}$I-prothrombin (8.0 nM; C) alone or in the presence of a 100-fold excess of the respective unlabelled protein. Specific binding is shown (mean±SEM of triplicate determinations). D-F. Dependence on concentration of Factors IX, X and prothrombin. PVC wells were incubated with recombinant calreticulin (9.1 fmoles/well), excess sites were blocked with blocking buffer, and then a binding assay was performed by adding the indicated concentration of either $^{125}$I-Factor IX (D), $^{125}$I-Factor X (E), or $^{125}$I-prothrombin (F) alone or in the presence of a 100-fold excess of the respective unlabelled protein. Specific binding is plotted versus free/added $^{125}$I-labelled clotting factor (either Factor IX, X or prothrombin). Data were analyzed by the nonlinear least-squares program, and the curve indicates the best fit line. Parameters of binding were for panel D, Kd=2.73±0.36 nM and N=21.8±1.13 fmoles/well; for panel E, Kd=3.24±0.69 nM and N=32.9±2.44 fmoles/well; and for panel F, Kd=8.26±0.52 nM and N=27.6±0.91 fmoles/well. The inset shows Scatchard analysis of the same data.

FIG. 7. Competitive binding study: effect of unlabelled Factors IX, X and prothrombin on the binding of $^{125}$I-Factor IX to recombinant calreticulin. Wells were incubated with calreticulin (9.1 fmoles/well) for 15 hrs at 4° C., excess sites in the wells were blocked with albumin-containing buffer, and then a binding assay was performed by adding three different concentrations of $^{125}$I-Factor IX (circle=6 nM; square=3 nM; triangle=1.5 nM) in the presence of the indicated concentrations of either unlabelled Factor IX (A), unlabelled Factor X (B), or unlabelled prothrombin (C). Inset, Dixon plot showing 1/Bound (1/B, fmole$^{-1}$) versus protein added (nM).

FIG. 8. Interaction of $^{125}$I-Factor IX with the N-domain, P-domain and C-domain of calreticulin. A. Wells were incubated with the indicated recombinant domain of calreticulin or glutathione-S-transferase control protein (0.5 μg/well) for 15 hr at 4° C., excess sites in the wells were blocked with albumin-containing buffer, and then a binding assay was performed with $^{125}$I-Factor IX alone (6.3 nM) or in the presence of a 100-fold molar excess of unlabelled protein. Specific binding is plotted versus the calreticulin domain (N, P or C) used in the assay (mean±SEM of triplicate determinations). B-D. Binding of $^{125}$I-Factors IX, X and prothrombin to the C domain of calreticulin. Wells were incubated with C domain (0.5 μg/well) for 15 hr at 4° C., excess sites were blocked with blocking buffer, and then a binding assay was performed with the indicated concentrations of either $^{125}$I-Factor IX (B), $^{125}$I-Factor X (C) or $^{125}$I-prothrombin (D) alone or in the presence of a 30-fold excess of the unlabelled respective protein. Specific binding is plotted versus the concentration of free/added tracer. Data were analyzed by the nonlinear least-squares program, and the curve indicates the best fit line. Parameters of binding were for panel B, Kd=2.2±0.5 nM and N=19.5±1.69 fmoles/well; for panel C, Kd=5.00±0.74 nM and N=39.7±2.72 fmoles/well; and for panel D, Kd=4.79±0.83 nM and N=20.7±1.49 fmoles/well. The inset shows Scatchard analysis of the same data.

FIG. 9. Infusion of recombinant rabbit calreticulin into mice. A. Removal of infused $^{125}$I-calreticulin from the plasma. Mice were infused via the tail vein with $^{125}$I-calreticulin (0.43 μg/animal), and at the indicated times blood was withdrawn for determination of radioactivity. The solid line represents the best fit to the data using the weighted least squares non-linear regression procedure. B. Removal of infused $^{125}$I-albumin from the plasma. Mice were treated as in (A), except that $^{125}$I-albumin (0.34 μg/animal) was used in place of $^{125}$I-calreticulin.

FIG. 10. Effect of calreticulin on coronary thrombosis in a canine model. Following instrumentation of the left circumflex artery, current was applied to the needle electrode until a 50% increase in mean blood flow velocity occurred (this corresponds to a ≈50% decrease in cross-sectional luminal area). The current was then turned off, a bolus of the indicated amount of calreticulin or saline was given into the left circumflex (in each case, volume was 0.5 ml), and vessel patency was monitored as described in the text.

FIG. 11. Binding of calreticulin to ECs. A. Dose-dependence. Confluent monolayers of bovine aortic endothelial cells (passage 6; 0.32 cm$^2$/well)(ECs) were incubated with the indicated concentration of $^{125}$I-calreticulin alone or in the presence of 100-fold excess of unlabelled protein. Monolayers were washed, bound radioactivity was eluted, and specific binding is plotted versus the free/added concentration of $^{125}$I-calreticulin. Data were analyzed by nonlinear least squares analysis, and the curve indicates the best-fit line. Parameters of binding were Kd=7.88±0.84 nM and N=4.38±0.20 fmoles/well. B. Competitive binding study of $^{125}$I-calreticulin binding to endothelium: effect of unlabelled C-domain. EC monolayers were incubated with $^{125}$I-calreticulin alone (6.3 nM) or in the presence of an 100-fold excess of either unlabelled calreticulin, C-domain, N-domain, and P-domain. Specific binding, the mean±SEM of triplicate determinations is shown.

Figure 12:
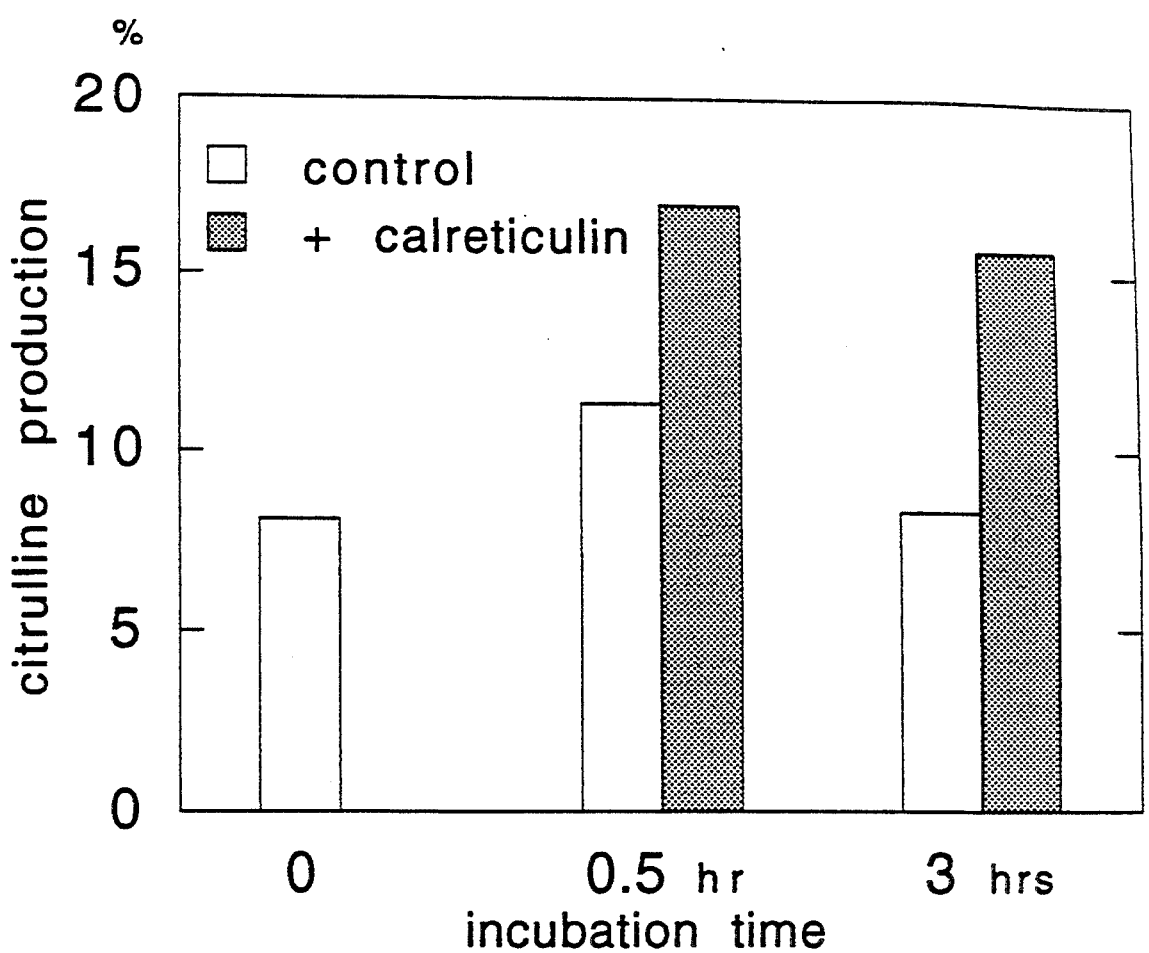
FIG. 12. Effect of calreticulin on EC nitric oxide synthase activity.

FIG. 12. Effect of calreticulin on EC nitric oxide synthase activity. Cultured ECs (3×10$^6$ cells/point) were incubated for the indicated time with calreticulin (380 nM), and then the citrulline assay was performed as described in the text.

LIST OF REFERENCES

1. Rapaport, S., In *Physiological Basis of Medical Practice*, Ed., West, J. pp. 385–404. 12th edition, Williams and Wilkins, Baltimore, 1990.

2. Gurewich, V., Nonn, T., and Lipinski, B. (1979) Thromb. Res. 14:931–940.

3. Gitel, S., Stephenson, R., and Wessler, S. (1977) PNAS(USA) 74:3028–3032.

4. Benedict, C., Ryan, J., Wolitzky, B., Ramos, R., Gerlach, M., Tijburg, P., and Stern, D. (1991) J. Clin. Invest. 88:1760–1765.

5. Thompson, A. (1986) Blood 67:565–572.

6. Stern, D., Knitter, G., Kisiel, W., and Nawroth, P. (1987) Brit. J. Haematol. 66:227–232.

7. Heimark R., and Schwartz, S. (1983) Biochem. Biophys. Res. Commun. 111:723-731.

8. Stern, D., Drillings, M., Nossel, J., Hurlet-Jensen, A., LaGamma, K., and Owen, J. (1983) PNAS(USA) 81:913-917.

9. Ahmad, S., Rawala-Sheikh, R., Ashby, B., and Walsh, P. (1989) J. Clin. Invest. 84:824-828.

10. Toomey, J., Smith, K., Roberts, H., and Stafford, D. (1992) Biochem. 31:1806-1808.

11. Toomey, J., Smith, K., and Stafford, D. (1991) J. Biol. Chem. 266:19198-19202.

12. Astermark, J., Bjork, I., Ohlin, A., and Stenflo, J. (1991) J. Biol. Chem. 266:2430-2437.

13. Derian, C., VanDusen, W., Przysiecki, C., Walsh, P., Berkner, K., Kaufman, R., and Friedman, P. (1989) J. Biol. Chem. 264:6615-6618.

14. Ryan, J., Wolitzky, B., Heimer, E., Lambrose, T., Felix, A., Tam, J., Huang, L., Nawroth, P., Wilner, G., Kisiel, W., Nelsestuen, G., and Stern, D. (1989) J. Biol. Chem. 264:20283-20287

15. Rimon, S., Melamed, R., Savion, N., Scott, T., Nawroth, P. and Stern, D. (1987) J. Biol. Chem. 262:6023-6031.

16. London, F., and Walshi, P. (1992) Circ. (Suppl. I) 86:#1855.

17. Fujikawa, K., Thomspon, A., Legaz, M., and Davie, E. (1974) Biochem. 12:4938-4945.

18. Fujikawa, K., Legaz, M., and Davie, E. (1972) Biochem. 11:4882-xxx.

19. Downing, M., Butkowski, R., Clark, M., and Mann, K. (1975) J. Biol. Chem. 250:8897-8906.

20. David, G., and Reisfeld, R. (1974) Biochem. 13:1014-1029.

21. Stern, D., Nawroth, P., Kisiel, W., Vehar, G., and Esmon, C. (1985) J. Biol. Chem. 260:6717-6722.

22. Smith, D., and Johnson, K. (1988) Gene (Amst.) 67:31-40.

23. Bakshi, S., and M. Michalak. (1991) J. Biol. Chem. 266:21458-21465.

24. Milner, R., Baksh, S., Shemanko, C., Carpenter, M., Smillie, L., Vance, J., Opas, M., and Michalak, M. (1991) J. Biol. Chem. 266:7155-7165.

25. Klotz, I., and Hunston, D. (1984) J. Biol. Chem. 258:11442-11445.

26. Segel, I. (1975) *Enzyme Kinetics*, pp. 100-106, John Wiley and Sons, New York.

27. Lollar, P., Hoak, J., and Owen, W. (1980) J. biol. Chem. 255:10279-10283.

28. Laemmli, U. (1970) Nature 227:680-685.

29. Bauw, G., VanDamme, J., Puype, M., Vanderkerckhove, J., Gesser, B., Ratz, G., Lauridsen, J., and Celis, J. (1989) PNAS(USA) 86:7701-7705.

30. Hewick, R., Hunkapiller, M., Hood, J., and Dreyer, W. (1981) J. Biol. Chem. 256:7990-7997.

31. Hunkapliier, M., Granlund-Moyer, K., and Whitely, N. (1986) in *Methods of Protein Microcharacterization* (Shively, J, Ed.) pp. 315-327, Humana Press, N.J.

32. VanDieijen, G., G. Tans, J. Rosing, and H. Hemker (1981) J. Biol. Chem. 256:3433-3442.

33. Stern, D., Nawroth, P., Handley, D. and Kisiel, W. (1985) PNAS(USA) 82:2523-2527.

34. Rosing, J., Tans, G., Govers-Riemslag, J, Zwaal, R., and H. Henker, (1980) J. Biol. Chem. 255:274-283.

35. Tracy, P., Nesheim, M., and Mann, K. (1981) J. Biol. Chem. 256:743-751.

36. Ryan, J., Brett, J., Tijburg, P., Bach, R., Kisiel, W., and Stern, D. (1992) Blood 80:966-974.

37. Nawroth, P. and Stern, D. (1986) J. Exp. Med. 163:740-745.

38. Stern, D., Nawroth, P., Harris, K., and Esmon, C. (1986) J. Biol. Chem. 261:713-718.

39. Choi, S., Fong, L., Kirven, M., and Cooper, A. (1991) J. Clin. Invest. 88:1173-1181.

40. Spady, D., Bilheimer, D., and Dietschy, J. (1983) PNAS(USA) 80:3499-3503.

41. Benedict, C., Mathew, B., Rex, K., Cartwright, J., and Sordahl, L. (1986) Circ. Res. 58:58-67.

42. Stuehr, D., Cho, H., Kwon, M., Weise., and Nathan, C. (1991) PNAS(USA) 88:7773-7777.

44. Esmon, N., Owen, W., and Esmon, C. (1982) J. Biol. Chem. 257:859-864.

45. Schmidt, A-M, Vianna, M., Gerlach, M., Brett, J., Ryan, J., Kao, J., Esposito, C., Hegarty, H., Hurley, W., Clauss, M., Wang, F., Pan, Y-C., Tsang, T., and Stern, C. (1992) J. Biol. Chem. 267:14987-14997.

46. Fliegel, L., Burns, K., MacLennan, D., Reithmeier, R., and Michalak, M. (1989) J. Biol. Chem. 264:21522-21528.

47. Rokeach, L., Haselby, J., Meilof, J., Smeenk, R., Unnasch, T., Greene, B., Hoch, S.(1991) J. Immunol. 147:3031-3039.

48. Collins, J., Xi, Z., Alderson-Lang, B., Treves, S., and Volpe, P. (1989) Biochem. Biophys. Res. Commun. 164:575-579.

49. Van, P., Peter, F., Seeling, J., (1989) J. Biol. Chem. 264:17494-17501.

50. Michalak, M., Milner, R., Burns, K., and Opas, M. (1992) Biochem. J. 285:681-692.

51. Sueyoshi, T., McMullen, B., Marnell, L., Du Clos, T., and Kisiel, W. (1991) Thromb. Res. 63:569-575.

---

What is claimed is:

1. A pharmaceutical composition, which comprises an amount of calreticulin effective for blocking or preventing thrombosis in a subject, causing substantially no defect or no defect in normal hemostasis, and a pharmaceutically effective carrier.

2. A method for blocking or preventing thrombosis in a subject, comprising administering to the subject the pharmaceutical composition of claim 1.

3. The method of claim 2, wherein the administering is intracoronary or intravenous.

4. The method of claim 2, wherein the subject is a human.

5. The method of claim 4, wherein the human is a human at risk for thrombosis; a human who can receive antithrombotic agents but who has not had an effective response to said antithrombotic agents; or a human unable to receive said antithrombotic agents.

6. The method of claim 5, wherein the human unable to receive said antithrombotic agents is a human undergoing intracranial surgery, or a human with a hemostatic defect.

7. The method of claim 4, wherein the administration is intracoronary and the amount is from about ( 0.04 mg calreticulin)/(Kg human subject) to about (0.07 mg calreticulin)/(Kg human subject).

8. The method of claim 7, wherein the amount is from about (0.05 mg calreticulin)/(Kg human subject) to about 0.06 mg calreticulin)/(Kg human subject).

9. The method of claim 4, wherein the administration is intravenous and the amount is from about (0.2 mg calreticulin)/(Kg human subject) to about 0.4 mg calreticulin)/(Kg human subject).

10. The method of claim 9, wherein the amount is about (0.3 mg calreticulin)/(Kg human subject).

11. A method for enhancing the action of an antithrombotic agent which prevents clotting or dissolves clots which have already formed, which method comprises administering to a subject calreticulin in combination with said antithrombotic agent in an amount and proportion for enhancing the action of said antithrombotic agent, to prevent clotting or dissolve clots which have already formed.

12. The method of claim 11, wherein said antithrombotic agent is an antiplatelet agent.

13. The method of claim 11, wherein the administering is intracoronary or intravenous.

14. The method of claim 11, wherein said antithrombotic agent is an anticoagulant agent.

15. The method of claim 14, wherein the anticoagulant agent is heparin, warfarin, coumarin derivatives, thrombin inhibitors, or Factor Xa inhibitors.

16. The method of claim 11, wherein said other antithrombotic agent is an antifibrinolytic agent.

17. The method of claim 16, wherein the antifibrinolytic agent is streptokinase, tissue plasminogen activator, urokinase, or acylated plasmin.

18. The method of claim 13, wherein the subject is a human.

19. The method of claim 18, wherein the human is a human at risk for thrombosis; a human who can receive antithrombotic agents but who has not had an effective response to said antithrombotic agents; or a human unable to receive said antithrombotic agents.

* * * * *